US012763177B2

(12) United States Patent
Lim

(10) Patent No.: US 12,763,177 B2
(45) Date of Patent: Oct. 13, 2026

(54) INTEGRATED MANAGEMENT SERVER FOR DENTAL CHART AND METHOD USING THE SAME

(71) Applicant: DENCOMM INC., Seoul (KR)

(72) Inventor: Byung Joon Lim, Seoul (KR)

(73) Assignee: DENCOMM INC., Seoul (KR)

(*) Notice: Subject to any disclaimer, the term of this patent is extended or adjusted under 35 U.S.C. 154(b) by 13 days.

(21) Appl. No.: 18/763,334

(22) Filed: Jul. 3, 2024

(65) Prior Publication Data

US 2025/0014694 A1 Jan. 9, 2025

(30) Foreign Application Priority Data

Jul. 4, 2023 (KR) ........................ 10-2023-0086481

(51) Int. Cl.
*G16H 10/60* (2018.01)
*G10L 15/26* (2006.01)
*G16H 10/20* (2018.01)

(52) U.S. Cl.
CPC ............. *G16H 10/60* (2018.01); *G10L 15/26* (2013.01); *G16H 10/20* (2018.01)

(58) Field of Classification Search
None
See application file for complete search history.

(56) References Cited

U.S. PATENT DOCUMENTS

2020/0135334 A1* 4/2020 Rajasekhar ............ G06N 3/084
2020/0367810 A1* 11/2020 Shouldice ............ A61B 5/4818
2023/0039451 A1* 2/2023 Lee ........................ G16H 40/20

(Continued)

FOREIGN PATENT DOCUMENTS

KR 10-20120052591 5/2012
KR 10-20160008982 1/2016
KR 10-2022-0095581 7/2022

OTHER PUBLICATIONS

"A Comparative Study on Support Vector Machine and Constructive RBF Neural Network for prediction of Success of Dental Implants"; A.L. I Oliveria, C. Baldissoretto, J. Baldissorretto; pp. 1015-1026 in Springer-Verlag Berlin Heidelberg 2005.

(Continued)

*Primary Examiner* — Jonathan Ng

(74) *Attorney, Agent, or Firm* — BACON & THOMAS, PLLC

(57) ABSTRACT

An integrated management server for a dental chart includes a memory storing instructions, and a processor. The instructions cause the processor to obtain a first script for speech of sounds generated during measurement of a patient's periodontal status to reflect the first script in a periodontal chart, provide features extracted from the periodontal chart to a pre-trained failure rate inference model to infer a failure rate for each implant type, obtain a second script for speech of sounds generated during discussions regarding a patient's implant type determined based on the inferred failure rate to reflect at least a portion of the first and second scripts in an implant chart, and obtain a third script for speech of sounds generated during discussions regarding an implant product to be used for the determined patient's implant type to reflect at least a portion of the first to third scripts in a laboratory chart.

19 Claims, 19 Drawing Sheets

(56) References Cited

U.S. PATENT DOCUMENTS

| | | | | |
|---|---|---|---|---|
| 2023/0170075 | A1* | 6/2023 | Alam | G02B 27/0172 705/2 |
| 2024/0029901 | A1* | 1/2024 | Ezhov | G16H 10/60 |
| 2024/0257807 | A1* | 8/2024 | Ganmukhi | G10L 15/22 |
| 2024/0355330 | A1* | 10/2024 | Lim | G10L 15/20 |
| 2025/0037834 | A1* | 1/2025 | Ng | G16H 10/20 |
| 2025/0132045 | A1* | 4/2025 | Okai | G16H 50/30 |
| 2025/0264307 | A1* | 8/2025 | Ebrahimi Afrouzi | G05D 3/10 |

OTHER PUBLICATIONS

"A Joint Speech Enhancement and Self-Supervised Representation Learning Framework for Noise-Robust Speech Recognition"; Qui-Shi Zhu, Jie Zhang, Zi-Qiang Zhang & Li-Rong Dai; IEEE/ACM Transactions on Audio, Speech and Language Processing, vol. 31, 2023.

* cited by examiner

Fig. 13

| # | Thumb Nail | CODE | Product Info. | Success Rate | Failure Rate | Counting Period | Number of Surgeries | Detail |
|---|---|---|---|---|---|---|---|---|
| ☐ | | IS34007AP | IS III ACTIVE IMPLANT, Regular Ø4.0 x 7.3mm | 98% | 2% | 49months | 50 | view |
| ☐ | | IS54007AP | IS III ACTIVE IMPLANT, Regular Ø5.0 x 7.3mm | 99% | 1% | 39months | 50 | view |
| ☐ | | IS84007AP | IS III ACTIVE IMPLANT, Regular Ø4.0 x 5.3mm | 95% | 5% | 89months | 51 | view |
| ☐ | | IS34017AP | IS III ACTIVE IMPLANT, Regular Ø4.0 x 3.3mm | 92% | 8% | 45months | 49 | view |
| ☐ | | IS34007BP | IS III ACTIVE IMPLANT, Regular Ø5.0 x 3.3mm | 88% | 11% | 40months | 50 | view |
| ☐ | | IS34087AP | IS III ACTIVE IMPLANT, Regular Ø4.0 x 5.3mm | 95% | 4% | 42months | 34 | view |
| ☐ | | IS34009AA | IS III ACTIVE IMPLANT, Regular Ø4.0 x 5.3mm | 91% | 8% | 45months | 56 | view |

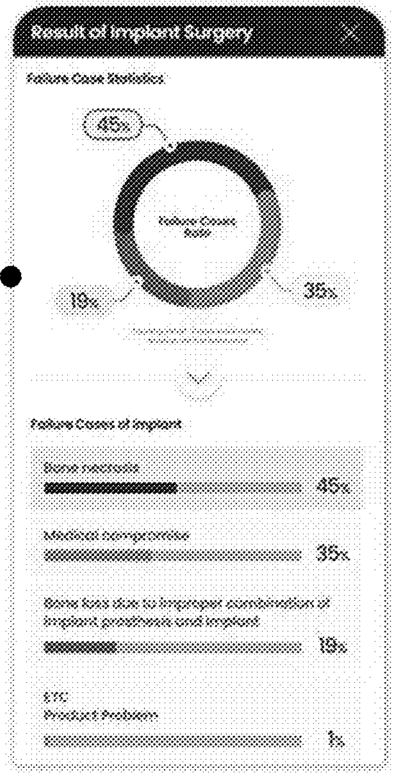

INTEGRATED MANAGEMENT SERVER FOR DENTAL CHART AND METHOD USING THE SAME

CROSS-REFERENCE TO RELATED PATENT APPLICATION

This non-provisional U.S. patent application is based on and claims priority under 35 U.S.C. § 119 of Korean Patent Application No. 10-2024-0086481 filed on Jul. 4, 2024, in the Korean Intellectual Property Office, the entire contents of which are hereby incorporated by reference.

BACKGROUND

1. Field

The present disclosure relates to an integrated management server for a dental chart and a method using the same.

2. Related Art

In dental practices, various charts are generated. For instance, in a dental clinic that performs implant procedures, charts such as a periodontal chart, an implant chart, or a laboratory chart may be created. The periodontal chart indicates the patient's periodontal health status. This chart may include various information such as bleeding from the gums, the degree of periodontal recession, or the spacing between teeth. Additionally, the implant chart may include the plan for which type of implant will be used for each patient. The laboratory chart may include information on which implant products will be used based on the type of implant determined for each patient.

The aforementioned charts are typically created by dental assistants who listen to the dentist's comments and manually input the information either on paper or into a computer. While smartphones or computers equipped with Speech-To-Text (STT) models are sometimes used for such chart creation, most of these STT models do not meet the expected accuracy levels. Consequently, these STT models are not widely adopted in dental practices at present.

Meanwhile, when establishing the implant plan to be recorded in the implant chart, various implant types are considered depending on the patient's periodontal condition or dental-related diseases. Since each patient's condition is different, the most suitable implant type for the patient is determined by the dental practitioners during the implant planning. If an inappropriate implant type is decided for the patient in the implant plan, it could potentially lead to medical accidents. Therefore, it is very important to determine the most suitable implant type for the patient.

Once the implant type to be used for a patient is determined, the specific implant product type is decided accordingly. When the procedure is performed, the stock of the implant products used in the procedure is depleted. Therefore, dental clinics order the necessary products from implant solution providers based on the level of product depletion. If orders are not placed in a timely manner, the required implant procedure for the next patient may not be carried out at the appropriate time.

SUMMARY

In view of the above, embodiments of the present disclosure provides a technique that facilitates the creation of various types of dental charts as described above.

Further, a type of implant to be placed in a patient may be recorded in an implant chart among these charts, embodiments of the present disclosure provides a technique that allows dental professionals or patients to consider the information about the failure rate for each of various implant types that is inferred and provided in the form of a report.

Furthermore, embodiments of the present disclosure provides a technique that ensures that an inventory of implant products to be held a dental clinic is maintained, taking into account the type of implant to be placed in the patient among various implant types.

It is to be understood, however, that the object of the present disclosure is not limited to those mentioned above.

In accordance with an aspect of the present disclosure, there is an integrated management server for a dental chart. The server includes a memory that stores one or more instructions; and a processor, wherein the memory includes a speech-to-text (STT) model that, when sounds containing noises and speeches are obtained and a noise cancelling process is performed on the obtained sounds, executes a process of extracting and processing features from the sound with the noise cancelling process and the sound without the noise cancelling process and a process of obtaining scripts for the speeches, wherein the one or more instructions, when executed by the processor, cause the processor to perform operations including: providing sounds containing noises and speeches, which are generated during measurement of a periodontal status of a patient, to the STT model, and obtaining a first script for the speeches to reflect the first script in a periodontal chart, providing features extracted from the periodontal chart to a pre-trained failure rate inference model for each implant type to infer a failure rate for each of a plurality of different implant types, providing sounds containing noises and speeches generated during discussions regarding an implant type of the patient, which is determined based on the inferred failure rate, to the STT model, and obtaining a second script for the speeches to reflect at least a portion of the first script and the second script in an implant chart, and providing sounds containing noises and speeches, which are generated during discussions regarding an implant product including a prosthesis to be used for the determined implant type of the patient, to the STT model, and obtaining a third script for the speeches to reflect at least a portion of the first script, the second script, and the third script in a laboratory chart, and wherein in a fine-tuning process included in training of the STT model, multiple sounds containing noises and speeches that are generated during a dental treatment, and a script for each of the multiple sounds are used as training data.

Further, the noise cancelling process may be performed by a model that performs speech enhancement.

Further, in the process of extracting the features from the sound with the noise cancelling process and the features from the sound without the noise cancelling process, each of the sound with the noise cancelling process and the sound without the noise cancelling process may be converted into a spectrogram, and the features are extracted from the corresponding spectrogram by using a convolutional neural network.

Further, a weight may be assigned such that a relatively higher weight value is assigned to a part that is relatively similar and a relatively lower weight value is assigned to a part that is not relatively similar between the sound with the noise cancelling process and the sound without the noise cancelling process.

Further, an encoding part included in the STT model may obtain an encoding vector as a result of the processing, and the encoding part is trained using multiple sounds containing speeches and noises through a pre-training process included in the STT model.

Further, a decoding part included in the STT model may perform the process of obtaining the scripts for the speeches by decoding the obtained encoding vector, and in the fine-tuning process, a training is performed such that a difference between a result outputted from the decoding part and the scripts serving as the training data is minimized, the result being outputted in response to the encoding part being provided with the multiple sounds containing the noises and the speeches generated during the dental treatment.

Further, a connectionist temporal classification (CTC) loss may be used for the training performed to minimize the difference between the result outputted from the decoding part and the scripts serving as the training data.

Further, the one or more instructions, when executed by the processor, may cause the processor to provide, if the scripts includes a word that is not in a dictionary, three consecutive words including the word that is not in the dictionary to a trained word correction model, and wherein the word that is not in the dictionary is replaced with a word corrected by the trained word correction model.

Further, the failure rate inference model for each implant type may be trained to provide a contribution ratio of each cause of failure when there are two or more causes of failure for each implant type.

Further, the memory further may include an implant type recommendation model, and each time an implant type is determined for the patient, features extracted from the periodontal chart of the patient are used as input training data and the determined implant type for the patient is used as labeled training data to train the implant type recommendation model.

Further, when a periodontal chart is generated for a new patient from measurement of a periodontal status of the new patient, the failure rate inference model for each implant may be used to infer the failure rate for each of the plurality of different implant types type, and the implant type recommendation model is used to recommend an implant type for the new patient by using features extracted from the periodontal chart generated for the new patient, and a warning is issued regarding the recommended implant type for the new patient in response to a case where the failure rate inferred by the failure rate inference model for the implant type recommended to the new patient exceeds a predetermined threshold.

Further, an order for the implant product may be generated or not generated depending on types and quantities of implant products listed in the laboratory chart.

Further, statistics on types of implants placed in patients and the failure rate for each implant type may be generated for each dental clinic or an individual dentist in each dental clinic.

Further, each of the periodontal chart, the implant chart, and the laboratory chart may include an interface chart through which one of a plurality of items is selected according to voice input or content for the selected item is recorded by reflecting the voice input, and a reporting chart that is dependently generated based on the content of the interface chart.

Further, the memory stores a selection instruction for each of the plurality of items, and wherein the one or more instructions, when executed by the processor, cause the processor to select, when the selection instruction is recognized from a script obtained from the voice input, the item corresponding to the recognized selection instruction.

Further, the memory may store recognized selection instructions cumulatively each time the selection instruction is recognized, and wherein the one or more instructions, when executed by the processor, cause the processor to retrain the fine-tuning included in the training of the STT model using the cumulatively stored selection instructions.

In accordance with other aspect of the present disclosure, there is an integrated management method for a dental chart that is performed by an integrated management server for the dental chart including a memory that stores a speech-to-text (STT) model that, when sounds containing noises and speeches are obtained and a noise cancelling process is performed on the obtained sounds, executes a process of extracting and processing features from the sound with the noise cancelling process and the sound without the noise cancelling process and a process of obtaining scripts for the speeches, the integrated management method including: providing sounds containing noises and speeches, which are generated during measurement of a periodontal status of a patient, to the STT model, and obtaining a first script for the speeches to reflect the first script in a periodontal chart, providing features extracted from the periodontal chart to a pre-trained failure rate inference model for each implant type to infer a failure rate for each of a plurality of different implant types, providing sounds containing noises and speeches generated during discussions regarding an implant type of the patient, which is determined based on the inferred failure rate, to the STT model, and obtaining a second script for the speeches to reflect at least a portion of the first script and the second script in an implant chart, providing sounds containing noises and speeches, which are generated during discussions regarding an implant product including a prosthesis to be used for the determined implant type of the patient, to the STT model, and obtaining a third script for the speeches to reflect at least a portion of the first script, the second script, and the third script in a laboratory chart, and wherein in a fine-tuning process included in training of the STT model, multiple sounds containing noises and speeches that are generated during a dental treatment, and a script for each of the multiple sounds are used as training data.

Further, the noise cancelling process is performed by a model that performs speech enhancement.

In accordance with other aspect of the present disclosure, there is a non-transitory computer-readable storage medium that stores a computer program including one or more instructions that, when executed by a processor of a computer, cause the computer to perform steps in the integrated management method as claimed in claim 17

According to one embodiment, various types of charts generated in dental clinics can be easily created and managed using an advanced STT model. Additionally, information necessary for determining the contents to be recorded in these charts, such as information used to determine the type of implant to be applied to a patient, can be provided. Furthermore, various types of information that can be useful for dental professionals or implant solution providers can also be provided in the form of reports.

BRIEF DESCRIPTION OF THE DRAWINGS

FIG. 13 illustrates an example of a report in which success rates or failure rates for implant types are inferred and recorded according to one embodiment of the present disclosure.

DETAILED DESCRIPTION

The advantages and features of the embodiments and the methods of accomplishing the embodiments will be clearly understood from the following description taken in conjunction with the accompanying drawings. However, embodiments are not limited to those embodiments described, as embodiments may be implemented in various forms. It should be noted that the present embodiments are provided to make a full disclosure and also to allow those skilled in the art to know the full range of the embodiments. Therefore, the embodiments are to be defined only by the scope of the appended claims.

In describing the embodiments of the present disclosure, if it is determined that the detailed description of related known components or functions unnecessarily obscures the gist of the present disclosure, the detailed description thereof will be omitted. Further, the terminologies to be described below are defined in consideration of the functions of the embodiments of the present disclosure and may vary depending on a user's or an operator's intention or practice. Accordingly, the definition thereof may be made on a basis of the content throughout the specification.

Figure 1:
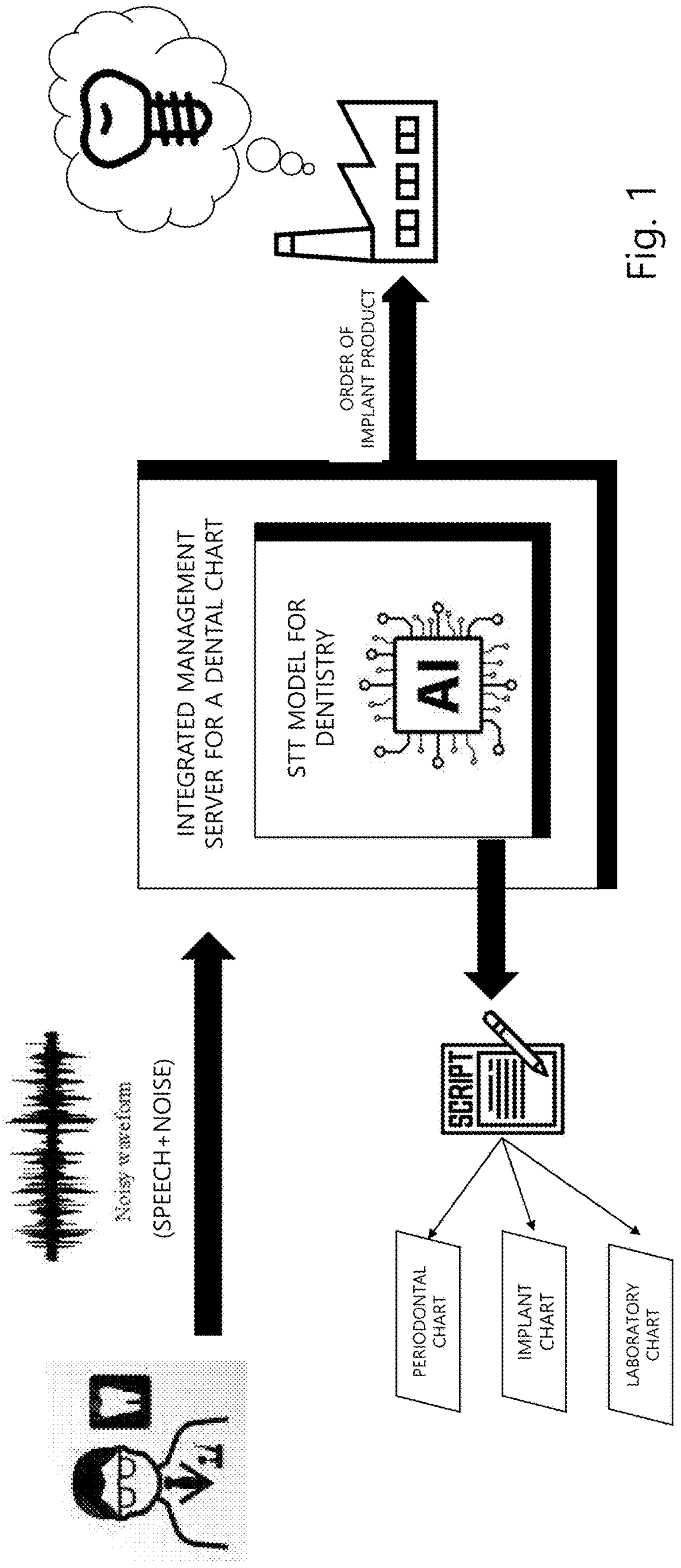
FIG. 1 conceptually illustrates a configuration in which dental charts are created and provided through an integrated management server for a dental chart, and implant products are ordered (placed) according to one embodiment of the present disclosure.

FIG. 1 conceptually illustrates a configuration in which dental charts are created and provided through an integrated management server for a dental chart, and implant products are ordered (placed) according to one embodiment of the present disclosure. However, it should be noted that FIG. 1 is merely an example to illustrate the technical scope of the present disclosure. Therefore, the present disclosure should not be construed as limited to those illustrated in FIG. 1.

Referring to FIG. 1, in a dental clinic, devices such as smartphones, smart pads, or PCs that include microphones and screens are provided. Sounds generated during dental treatment or discussion among dental practitioners are recognized by these devices. The recognized sounds are then transmitted to the integrated management server for the dental chart. These sounds may include both speech and background noise.

Among these, the speech may include conversations (spoken words) between dental practitioners, voice commands from the dental practitioners, or interactions between dental practitioners and patients. Additionally, the noise may include various sounds generated during the aforementioned conversations, voice commands, or dental treatments. For example, noise may arise from the operation of dental drills or dental suctions. Noise may also be generated when filling teeth with a predetermined substance. The noise may further include car horns from outside the dental clinic.

Thus, the aforementioned sounds may be in the form of a noisy waveform as shown in FIG. 1. In other words, the aforementioned sounds may include noise and speech.

These sounds are provided to the dental-specific STT (Speech-To-Text) model prepared within the integrated management server for the dental chart. Then, through the STT model for dentistry, the speech included in the sounds is recognized and outputted. The output can take many forms. For example, a text such as a script may be outputted as shown in FIG. 1, but is not limited thereto.

In one embodiment, the dental-specific STT model is trained to be robust to noise. For example, the dental-specific STT model is trained to accurately recognize and output the speech contained in the sounds while the noise is also generated during the dental treatment. That is, compared to a general STT model, the dental-specific STT model according to one embodiment may be trained to have a relatively high speech recognition rate despite the presence of significant noise.

Meanwhile, the techniques applied to the dental-specific STT model described above can also be applied to other medical fields. Specifically, depending on the type of training data used in a fine-tuning process, an STT model in association with pediatrics, obstetrics and gynecology, ophthalmology, or dermatology can also be implemented using the techniques according to the embodiment.

The scripted output from the dental-specific STT model can be utilized for generating various charts used in dentistry. For example, the scripted output can be employed to create or modify charts such as a periodontal chart, an implant chart, or a laboratory chart.

Here, the periodontal chart indicates the patient's periodontal health status. This chart may include various information such as bleeding from the gums, the degree of periodontal recession, or the spacing between teeth. Additionally, the implant chart may include the plan for which type of implant will be used for each patient. The laboratory chart may include information on which implant products will be used based on the type of implant determined for each patient.

Hereinafter, a process of creating each of the aforementioned charts will be described in detail with specific examples. During dental treatment with patient or discussions among dental practitioners, statements are made that may include voice (verbal) commands necessary for creating or modifying various charts. For instance, voice commands specifying the type of chart to be created, such as 'periodontal chart,' 'implant chart,' 'laboratory chart,' and the like, may be included in such statements. Alternatively, the statements may include voice representations of patient's personal information, such as 'patient name,' 'age,' '41,' and the like. Additionally, the statements may include information to be recorded in the chart, such as 'Diagnosis,' 'Tx. Plan,' 'Early Placement,' 'Anesthesia,' 'Block,' 'Bone Density,' 'D1,' and the like.

When text, such as a script, is output from the statements through the STT model according to one embodiment, an operation of creating or modifying a chart is performed based on this text. To facilitate this process, the integrated management server for the dental chart described above may include a module or a model designed to extract instructions (commands) related to chart creation or modification from the text, and operate to enable the functionality of creating or modifying charts based on the extracted commands.

In one embodiment, the various charts described above are interrelated. For example, the contents recorded in the implant chart may include at least some of the contents recorded in the periodontal chart. More specifically, considering that the implant plan among the contents recorded in the implant chart is determined by referring to the patient's periodontal status, information about the patient's periodontal status, i.e., at least some of the contents recorded in the periodontal chart, may be included in the implant chart as the basis for the implant plan. Similarly, the contents recorded in the laboratory chart may include at least some of the contents recorded in the periodontal chart or the implant chart. Considering that the type of implant product recorded in the laboratory chart is determined by referring to the type of implant to be operated on the patient, information about the implant type, i.e., at least some of the contents recorded in the implant chart, may be included in the laboratory chart as the basis for the decision on the type of implant product. Further, considering that the type of implant product may also be determined by the patient's condition described in the periodontal chart, at least some of the contents recorded in the periodontal chart may be included in the laboratory chart.

In one embodiment, various types of reports may be provided. For instance, dental practitioners may receive reports on the success rates or the failure rates of different types of implants, considering the condition of each patient. By referencing these inferred success or failure rates, dental practitioners can determine the most suitable and optimal type of implant for each patient.

Further, various reports may be provided to implant solution providers, such as companies involved in the research, development, production, or sale of implant products, including prosthetics corresponding to different implant types. These reports may include information on the usage rates of different types of implants, information on the success rates of different types of implants, information on the failure rates of different types of implants, and the preferred implant types of different dental clinics or dental practitioners. In addition, orders for implant products from various dental clinics may be provided to these companies. Based on these reports and orders, implant the solution providers may manage their inventory levels for products with high or low demand and determine the direction for new product research and development.

In other words, according to one embodiment, various types of charts generated in a dental clinic can be easily created and managed by an advanced STT model. Additionally, various types of information that may be useful for the dental practitioners or the implant solution providers can be provided in the form of reports. For example, information that can be referenced by the dental practitioners when determining the contents to be recorded in the aforementioned charts or information that can be referenced by the implant solution providers when determining R&D directions or managing inventory levels can be included in the reports.

Figure 2:
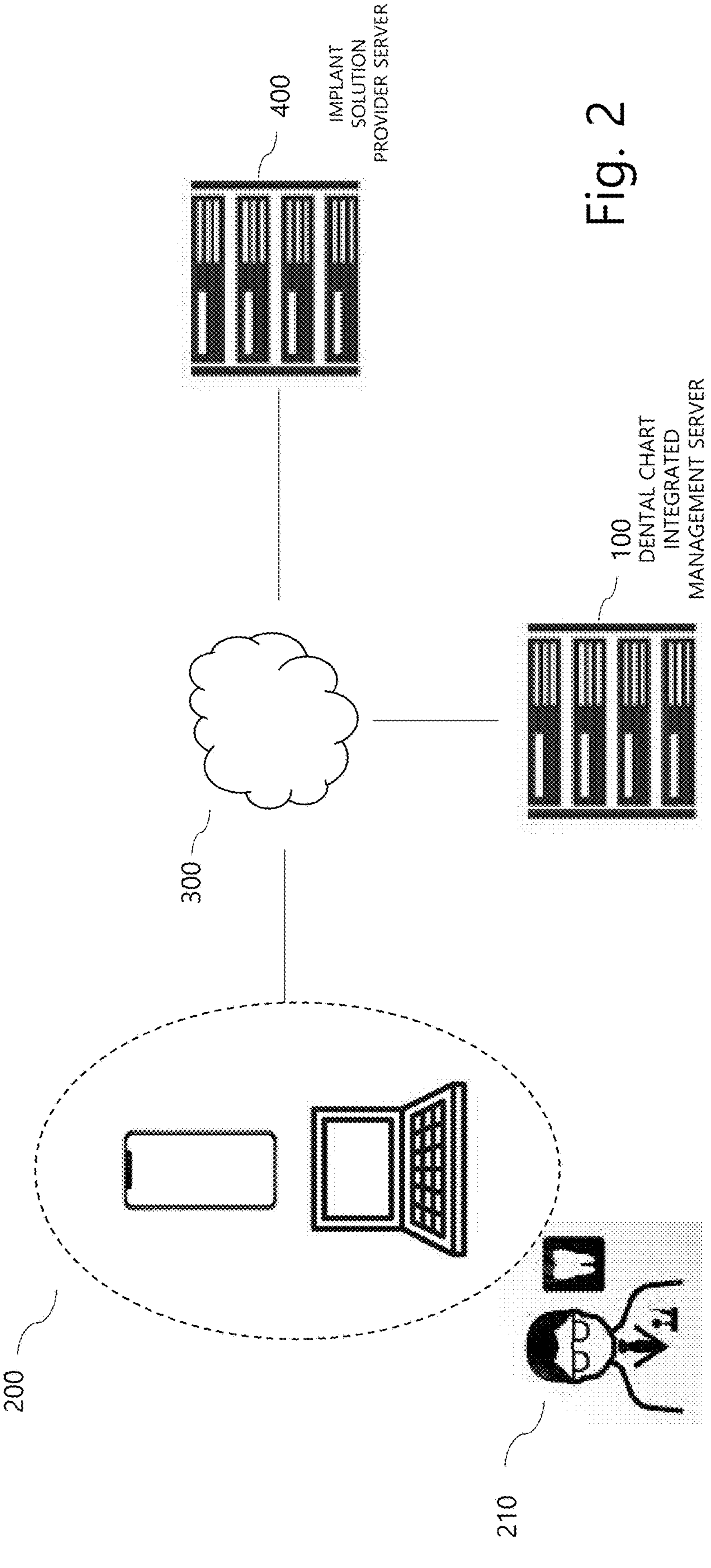
FIG. 2 illustrates an example of a configuration in which the integrated management server for the dental chart is connected on a network according to one embodiment of the present disclosure.

FIG. 2 illustrates an example of a configuration in which the integrated management server for the dental chart (hereinafter, also referred to as the "dental chart integrated management server") is connected on a network according to one embodiment.

Referring to FIG. 2, a dental chart integrated management server 100 according to one embodiment may be connected to a user terminal 200 or an implant solution provider server 400 through a network 300. Here, it should be noted that FIG. 2 is merely an example to illustrate the technical scope of the present disclosure. Therefore, the present disclosure should not be construed as limited to those illustrated in FIG. 2.

Here, the network 300 may be a wireless network or a wired network. The wireless network may include, for example, at least one of long-term evolution (LTE), LTE Advance (LTE-A), code division multiple access (CDMA), wideband CDMA (WCDMA), universal mobile telecommunications system (UMTS), wireless broadband (WiBro), wireless fidelity (WiFi), Bluetooth, near field communication (NFC), and global navigation satellite system (GNSS). The wired network may include, for example, at least one of universal serial bus (USB), high definition multimedia interface (HDMI), recommended standard 232 (RS-232), local area network (LAN), wide area network (WAN), Internet and telephone network.

Next, the user terminal 200 refers to a terminal (device) of a user who intends to use the dental chart integrated management server 100 or the solutions provided by such server 100. For example, the user terminal 200 may be a terminal device used by dental professionals or a terminal device used by a patient. Alternatively, the user terminal 200 may be a terminal of a third-party data provider who collects sounds containing speeches and noises that are generated in the dental clinic and builds medical big data from the collected sounds.

The user terminal 200, as shown in FIG. 2, may include a smartphone, a tablet PC, a desktop PC, or a server. However, the user terminal 200 is not limited thereto. Additionally, the user terminal 200 may be equipped with a speech recognition device such as a microphone, a display unit that displays charts, and a communication unit. The sounds generated in the dental clinic may be inputted to the user terminal 200 through the speech recognition device such as the microphone. Further, the communication unit may transmit the sounds inputted to the user terminal 200 to the dental chart integrated management server 100 through the network 300. When the speech (voice) included in these sounds is recognized, a chart can be created based on the recognized speech. The chart, either in the process of being created or as the final result, may be displayed on the display unit.

A server 400 for the implant solution providers refers to a server operated by companies that research, develop, produce, or sell implant solutions. This server 400 can be implemented using general computers or similar devices. The server 400 may include a communication unit, a display unit, and an input unit. Through the communication unit, the server 400 may receive purchase requests (orders) for specific implant products from the dental chart integrated management server 100. Through the display unit, a list of purchase requests received from the relevant company or various types of reports containing information generated by the dental chart integrated management server 100 may be displayed. However, the functions that can be implemented on the server 400 are not limited thereto.

The dental chart integrated management server 100 may receive all the sounds generated in the dental clinic. These sounds may originate from the dental clinic, but are not limited thereto. Additionally, these generated sounds may include speeches (voices) and noises. Here, since the speech and the noise have already been discussed, an additional description thereof will be omitted.

The dental chart integrated management server 100 may analyze the received sounds to recognize the speech only. The recognized speech may be then outputted in the form of text, such as a script (that is, the recognized speech is converted into text). More specifically, even if the noise is generated during the dental treatment, the dental chart integrated management server 100 is configured to accurately recognize the speech contained in the sounds and output the recognized speech in the form of a script. In other words, compared to a general STT model, even with the severe noise, the dental chart integrated management server 100 according to one embodiment can accurately recognize the speech and output the recognized speech in the form of the script.

Then, various types of charts are generated by the dental chart integrated management server 100. Specifically, when the aforementioned sounds are provided to the STT model and a first script for the speech is obtained, this first script is reflected in the periodontal chart.

Meanwhile, features may be extracted from the periodontal chart reflecting the first script. For feature extraction, a language model such as RNN, LSTM, or BERT, which is used to extract features from the input text, can be utilized. To this end, the aforementioned language model may be integrated into the dental chart integrated management server 100.

When features are extracted from the periodontal chart reflecting the first script, these features are used to infer the failure rate or the success rate for each of a plurality of different implant types. In this case, the extracted features reflect the overall condition of the patient, including the periodontal status of the patient receiving the implant. Therefore, the inferred failure rate or the inferred success rate indicates the probability of failure or success for each implant type, taking into account the condition of each patient.

The dental professionals may discuss and decide on the type of implant to be placed in the patient based on the inferred failure or success rate for each type of implant. In other words, in one embodiment, the inferred failure or success rate for each of the aforementioned types of implants may be taken into account in deciding on the type of implant to be placed in the patient, which is the most important part of the implant plan that will be documented in the implant chart.

Further, various information, i.e., the implant plan, including the type of implant thus determined is then recorded on the implant chart. Furthermore, conversations or discussions regarding the type of implant determined by the dental professionals can also be documented in the implant chart. For this purpose, the conversations or discussions may be processed by the STT (Speech-to-Text) model to obtain a second script for the speech, and the second script is then incorporated into the implant chart. Depending on the embodiment, at least some of the first script may additionally be reflected in the implant chart.

Further, the dental professionals may refer to the type of implant determined to be placed in the patient and discuss to determine the implant product that corresponds to the type of implant, such as the type, specification, or manufacturer of the prosthetic material. The conversations exchanged during these discussions may be processed by the STT model to obtain a third script for the speech. Subsequently, this third script, representing the conversations exchanged during the discussions, is incorporated into the laboratory chart. Depending on the embodiment, at least some of the first script or the second script may additionally be reflected in the laboratory chart.

In other words, according to one embodiment, the various types of charts generated in dentistry can be efficiently created or managed by an advanced STT model, and the information required to determine the contents of these charts can be provided as a reference for determining, for example, the type of implant to be placed in a patient.

Hereinafter, the dental chart integrated management server 100 will be described in more detail.

Figure 3:
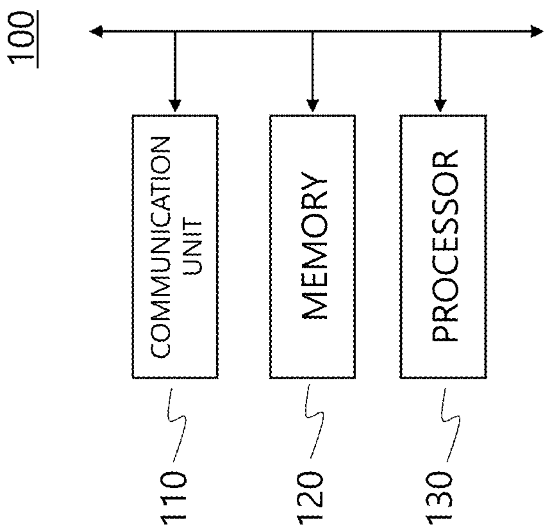
FIG. 3 schematically illustrates an example of a block diagram of the integrated management server for the dental chart according to one embodiment of the present disclosure.

FIG. 3 schematically illustrates an example of a block diagram of the dental chart integrated management server 100 according to one embodiment of the present disclosure. Referring to FIG. 3, the dental chart integrated management server 100 may include a communication unit 110, a memory 120, and a processor 130. However, a configuration shown in FIG. 3 is merely an example to illustrate the technical scope of the present disclosure. Therefore, the present disclosure should not be construed as limited to those in the configuration shown in FIG. 3. For example, the dental chart integrated management server 100 may include at least one component that is not shown in FIG. 3 or may not include at least one component shown in FIG. 3.

The communication unit 110 may be implemented by a wired communication module or a wireless communication module. The dental chart integrated management server 100 may communicate with external terminals, such as the various types of user terminals 200 or the server 400 shown in FIG. 2, through the communication unit 110.

The memory 120 may be implemented by an information storage medium. The information storage media may include at least one of a flash memory, a hard disk, a multimedia card micro type memory, a card type memory (e.g., an SD memory, an XD memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disk, an optical disk and/or the like. However, the information storage media is not limited thereto.

The memory may store various kinds of information. For example, the memory 120 may store information obtained by the dental chart integrated management server 100 from external terminals such as the user terminals 200 or the like through the communication unit 110. Further, the memory 120 may store a plurality of training data that may be utilized for training various types of models or modules to be described later.

In addition, the memory 120 may have various types of modules or models implemented therein. When such modules or models are executed by the processor 130 to be described later, desired functions are performed. Each of the modules or the models will be described later.

Next, the processor 130 will be described in detail. First, the processor 130 according to one embodiment may execute at least one instruction stored in the memory 120 to perform technical features according to one embodiment of the present disclosure that will be described later.

In one embodiment, the processor 130 may include at least one core. Further, the processor 130 may include a central processing unit (CPU), a general purpose graphics processing unit (GPGPU), a tensor processing unit (TPU), or the like to perform data analysis and/or data processing.

The processor 130 may train a neural network or a model that is designed using a machine learning or a deep learning. To this end, the processor 130 may perform computations necessary for training the neural network, including processing input data for training, extracting features from the input data, calculating errors, and updating the weights of the neural network using backpropagation.

The processor 130 may also perform inference for a predetermined purpose by using a model implemented in an artificial neural network method.

Hereinafter, an artificial neural network will be described. A model in the specification may indicate any type of computer program that operates based on a network function, an artificial neural network, and/or a neural network. In the specification, the terms "model," "neural network," "network function," and "neural network" may be used interchangeably. In the neural network, one or more nodes are interconnected through one or more links to form an input node and output node relationship in the neural network. Characteristics of the neural network may be determined based on the number of nodes and links, the connections between the nodes and the links, and the weight assigned to each link in the neural network. The neural network may be composed of a set of one or more nodes. A subset of the nodes that make up the neural network may constitute a layer.

Figure 4:
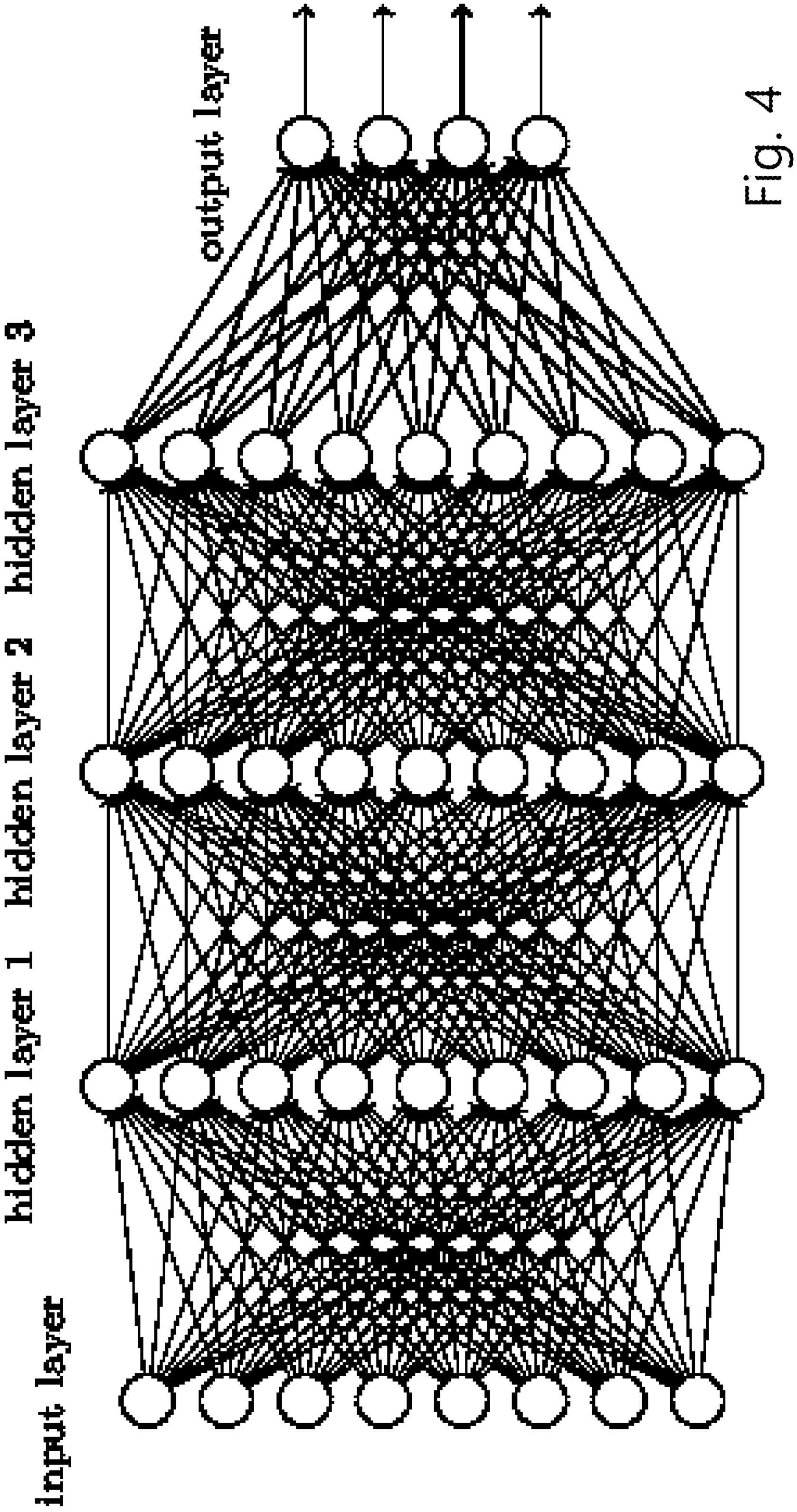
FIG. 4 conceptually illustrates a deep learning architecture.

Among neural networks, a deep neural network (DNN) may refer to a neural network that includes a plurality of hidden layers in addition to an input layer and an output layer. As shown in FIG. 4 that illustrates the concept of having intermediate hidden layers in the deep neural network, the deep neural network may include one or more, preferably two or more, hidden layers.

The deep neural network may include a convolutional neural network (CNN), a recurrent neural network (RNN), a long short-term memory (LSTM) network, a generative pre-trained transformer (GPT), an autoencoder, a generative adversarial network (GAN), a restricted boltzmann machine (RBM), a deep belief network (DBN), a Q network, a U network, a Siamese network, a transformer, and the like.

The deep neural network described above may be trained using a transfer learning method. In the transfer learning method, a pre-training process and a fine-tuning process are performed.

Here, in the pre-training process, a large amount of unlabeled training data is used to train the model to be suitable for the first task. As a result, a pre-trained model (or base model) is obtained.

Further, in the fine-tuning process, labeled training data is used to train the model to be suitable for the second task using supervised learning. As a result, the desired final model is obtained through the transfer learning method.

Examples of models trained with this transfer learning approach include, but are not limited to, bidirectional encoder representations from transformers (BERT).

The neural network, including the deep neural network described above, may be trained to minimize output errors. In the training process of the neural network, the training data are repeatedly inputted to the neural network. Then, the output of the neural network for the training data is compared with the target output, and the error therebetween is calculated. The error is then backpropagated from the output layer to the input layer of the neural network, updating the weights of each node in the neural network to reduce the error.

Meanwhile, the model according to one embodiment may be implemented by adopting at least a portion of a transformer architecture. Here, the transformer may include an encoder that encodes embedded data and a decoder that decodes the encoded data. The transformer may have a structure that receives a sequence of data and outputs a sequence of data of different types through encoding and decoding steps. In one embodiment, the sequence of data may be processed and prepared into a form operable by a transformer. The process of processing the sequence of data into a form operable by the transformer may include an embedding process. Representations such as data tokens, embedding vectors, and embedding tokens may refer to the embedded data in the form that can be processed by the transformer.

In order for the transformer to encode and decode the sequence of data, the encoders and the decoders within the transformer may utilize an attention algorithm. Here, the attention algorithm refers to an algorithm that that calculates the similarity between one or more keys and a given query, reflects this similarity onto the corresponding values associated with each key, and computes an attention value by taking a weighted sum of the values that have been adjusted based on the calculated similarity.

Depending on how the query, keys, and values are set, various types of attention algorithms can be classified. For example, when the query, keys, and values are all set to be the same to obtain the attention, it can refer to a self-attention algorithm. On the other hand, in order to process a sequence of input data in parallel, the embedding vectors can be dimensionally reduced, and individual attention heads can be obtained for each partitioned embedding vector. This approach is known as multi-head attention algorithm.

In one embodiment, a transformer may include modules that perform multiple multi-head self-attention algorithms or multi-head encoder-decoder algorithms. Additionally, the transformer in one embodiment may include additional components such as embedding, normalization, or softmax, apart from attention algorithms. The method of constructing the transformer using attention algorithms may include the approach described in "Attention Is All You Need" by Vaswani et al., presented at the 2017 NIPS conference, which is hereby incorporated by reference.

The transformer can be applied to various data domains, including embedded natural language, segmented image data, or audio waveforms. As a result, the transformer can convert a sequence of input data into a sequence of output data. Data with different data domains can be transformed to be processed by the transformer, which is referred to as embedding.

Moreover, the transformer can process additional data that represents the relative positional relationships or phase relationships between a sequence of input data. Alternatively, the sequence of input data may be embedded with additional vectors representing the relative positional relationships or phase relationships between the input data. In one example, the relative positional relationships between the sequence of input data may include, but is not limited to, the word order within a natural language sentence, the relative positions of segmented images, or the temporal order of segmented audio waveforms. The process of incorporating information that represents the relative positional relationships or phase relationships between the sequence of input data is referred to as positional encoding.

Hereinafter, various operations or functions that the dental chart integrated management server 100 may perform by executing at least one instruction stored in the memory 120 by the processor 130 will be described.

First, the processor 130 may control the communication unit 110. Thereafter, the dental chart integrated management server 100 may obtain information by performing communication with the user terminal 200 or the server shown in FIG. 2 through the communication unit 110.

The processor 130 may also read the aforementioned data or instructions stored in the memory 120, and may write new data or instructions to the memory 120. Additionally, the processor 130 may modify or delete data or instructions that have already been written.

Figure 5:
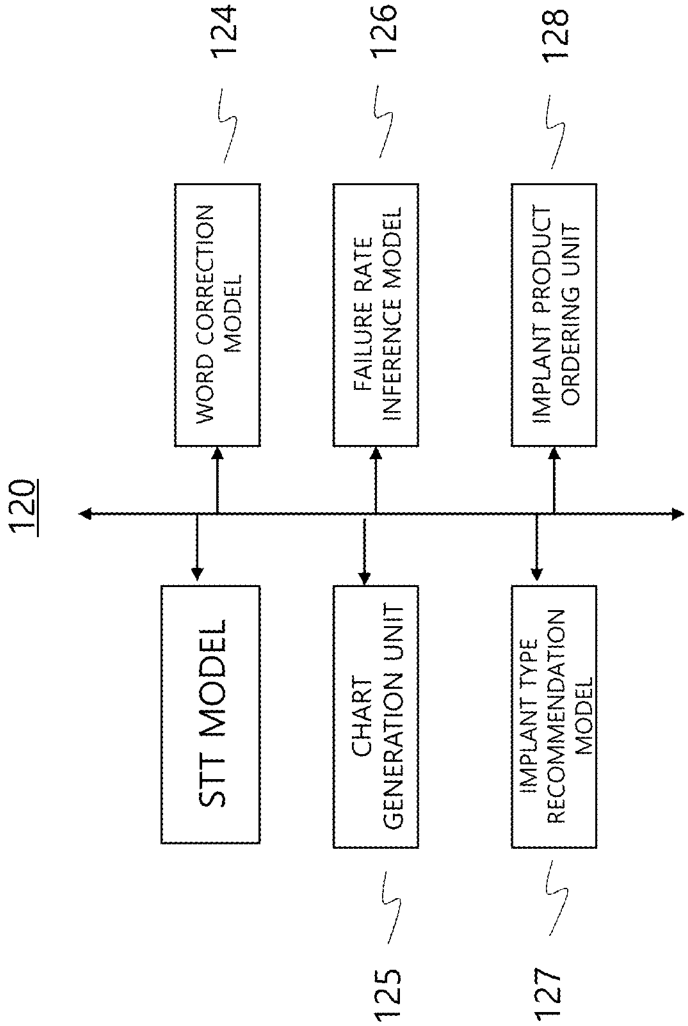
FIG. 5 conceptually illustrates various types of models or modules implemented according to one embodiment of the present disclosure.

Further, the processor 130 may execute various models or modules stored in the memory 120. Here, these models or modules may be implemented by the above-described artificial neural network method or a rule-based method. Examples of such models or modules may include the STT model, a word correction model 124, a chart generation unit 125, a failure rate inference model 126, an implant type recommendation model 127, and an implant product ordering unit 128, as illustrated in FIG. 5. However, these models or modules are not limited to those depicted in FIG. 5.

First, the STT model shown in FIG. 5 will be described in more detail. Such an STT model may be designed specifically for use in dentistry. Specifically, the STT model according to one embodiment may be implemented by the transformer. More specifically, the STT model may be implemented by a sequence-to-sequence transformer. The sequence-to-sequence transformer differs from the conventional transformer in that a decoder-encoder attention is used in a decoder.

Figure 6:
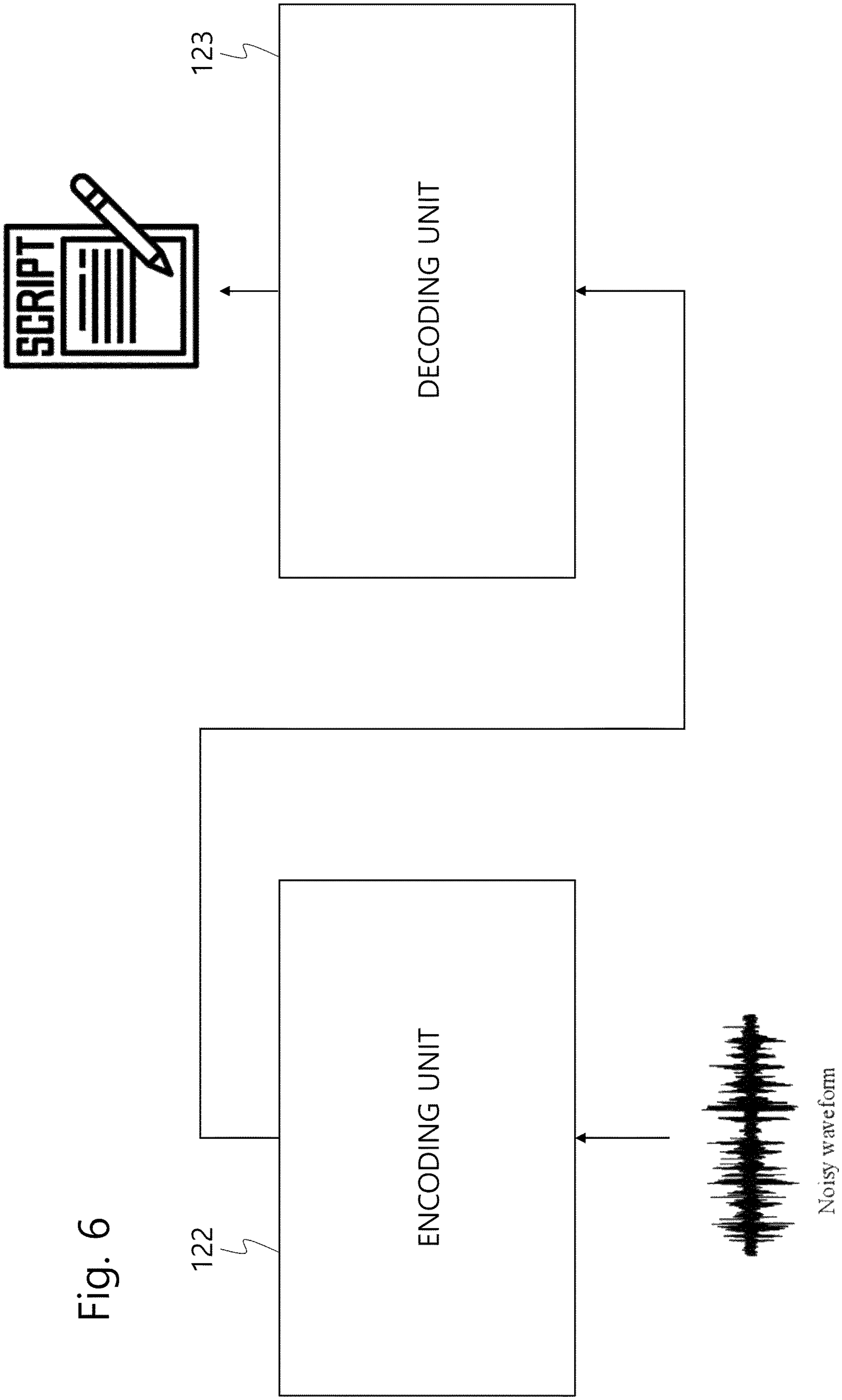
FIG. 6 conceptually illustrates an architecture of an STT model implemented according to one embodiment of the present disclosure.

The STT model may include an encoding part 122 and a decoding part 123 as shown in FIG. 6, but is not limited thereto.

The encoding part 122 is configured to receive and encode a sound, specifically a noisy waveform, which contains speech and noise. The decoding part 123 is configured to receive an encoding vector from the encoding part 122, convert the encoding vector into text such as a script, and output the converted text. That is, when the aforementioned sound is provided to the encoding part 122, the encoding part 122 generates the encoding vector. The encoding vector thus generated is then provided to the decoding part 123. Subsequently, the decoding part 123 utilizes the received encoding vector to generate and output a script corresponding to the speech contained in the sound.

Figure 7:
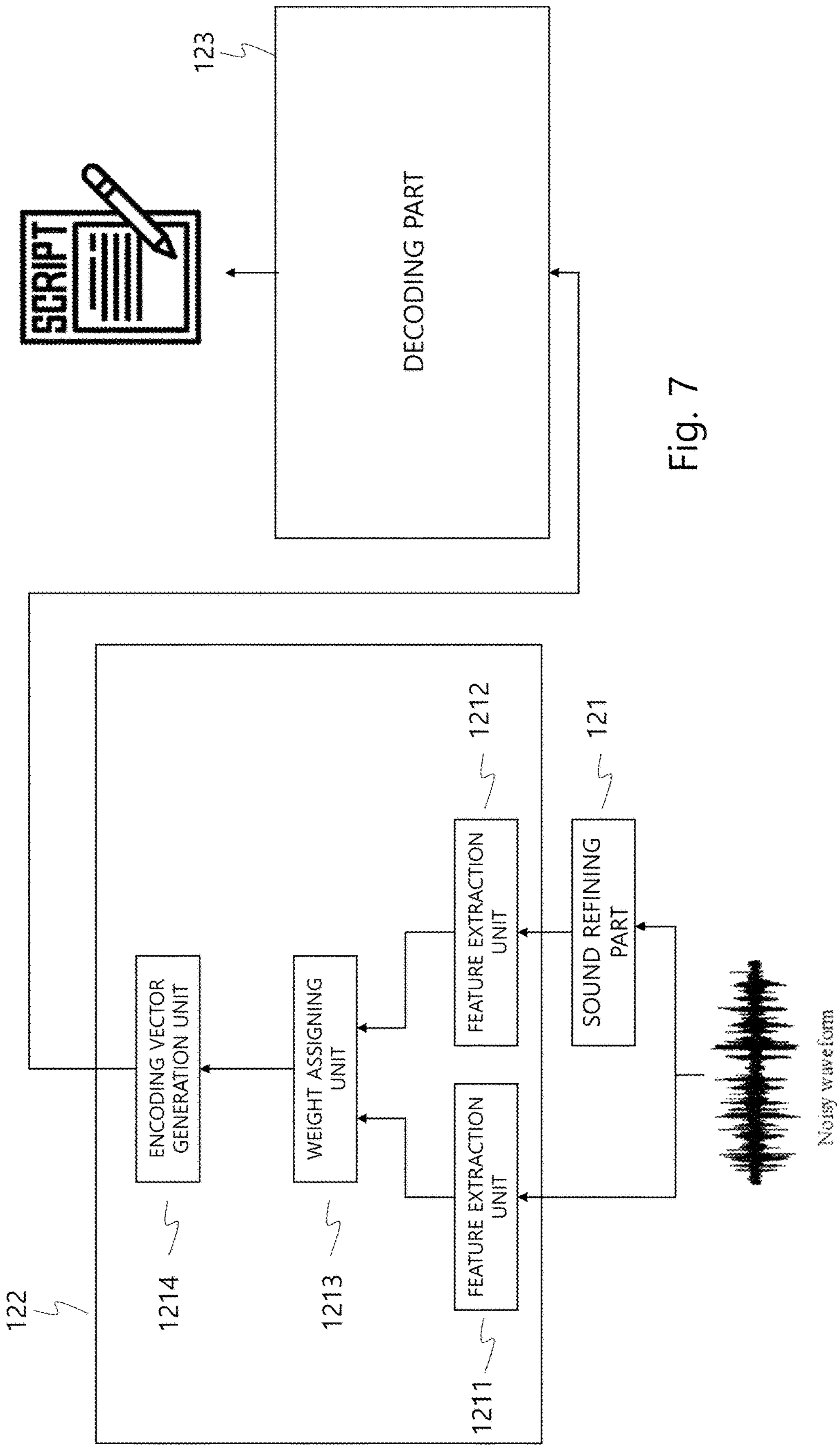
FIG. 7 conceptually illustrates an architecture of an STT model implemented according to another embodiment of the present disclosure.

Meanwhile, the architecture of the STT model according to one embodiment is not limited to that shown in FIG. 6. For example, the STT model may be implemented in the form of the architecture shown in FIG. 7. Referring to FIG. 7, the STT model may be implemented to mainly include a sound refining part 121, the encoding part 122, and the decoding part 123. In FIG. 7, the encoding part 122 may be configured to include, but is not limited to, feature extraction units 1211 and 1212, a weight assigning unit 1213, and an encoding vector generation unit 1214.

Hereinafter, the configuration of FIG. 7 will be described in more detail. The sound refining part 121 is configured to cancel the noise contained in the sound. The sound refining part 121 may be implemented by a model that performs speech enhancement. The speech enhancement refers to a technique for clarifying speech signals contained in the sound.

Various techniques may be used in the speech enhancement. For example, in the speech enhancement, at least one of spectral subtraction, Wiener filtering, and adaptive filtering, but not limited thereto, may be performed.

Among these, the spectral subtraction refers to one of the techniques for removing background noise from the sound. Specifically, when the spectral subtraction is applied, a frequency spectrum of a speech signal and a spectrum of background noise are analyzed, and then a signal component in a frequency band where the noise is present is reduced. Therefore, the background noise can be reduced, and thus the speech signal can be clear.

Further, the Wiener filtering also refers to one of the techniques for removing noise from the sound. Specifically, in the Wiener filtering, the statistical properties of the speech signal and the noise signal are analyzed, and then the noisy part is removed. Thus, the speech signal can be clear. The Wiener filtering can be applied in the time domain or the frequency domain. The Wiener filtering is more effective when used in conjunction with other filtering techniques.

Lastly, the adaptive filtering is one of the techniques used to remove noise from the speech signal and improve the quality of the speech signal. Specifically, in the adaptive filtering, the noise is separated from the speech signal by adjusting filtering weights in real time to thereby easily remove the noise.

To the encoding part 122, the sound containing speech and noise and also the result of a process in which the noise has been cancelled from the sound are inputted. In other words, the noise cancelling sound as well as the sound that is a recognition target are inputted to the encoding part 122.

Then, a feature is extracted from each of the feature extraction units 1211 and 1212 included in the encoding part 122. Specifically, the feature extraction unit 1211 may extract a feature from the sound on which the noise cancelling process has not been performed. Further, the feature extraction unit 1212 may extract a feature from the sound on which the noise cancelling process has been performed. Unlike the encoding part 122 shown in FIG. 7 that includes the two feature extraction units 1211 and 1212, the encoding part 122 may include a single feature extraction unit. In this case, the single feature extraction unit may extract both of a feature from the sound without the noise cancelling process and a feature from the sound with the noise cancelling process.

The two extracted features may be different from each other since one feature is extracted from the sound with the noise cancelling process while the other feature is extracted from the sound without the noise cancelling process. If these two features are compared in terms of frequency, there may be identical parts and non-identical parts. The identical parts indicate parts of the sound that are not affected by the noise or are relatively less affected by the noise, and the non-identical parts indicate parts of the sound that are affected by the noise or are relatively more affected by the noise. The identical parts and the non-identical parts can be used in a learning process called feature sharing.

Next, the feature extraction units 1211 and 1212 will be described in more detail. As described above, each of the feature extraction units 1211 and 1212 receives the sound. Then, each of the feature extraction units 1211 and 1212 converts this input sound into a spectrogram. That is, in each of the feature extraction units 1211 and 1212, the sound signal is transformed into a frequency domain. The transformation may use a technique such as, but not limited to, the short-time Fourier transform (STFT). Then, the feature is extracted from the spectrogram in each of the feature extraction units 1211 and 1212. For feature extraction, a feature extraction technique used in convolutional neural network (CNN) may be used, but is not limited thereto.

The two features from the feature extraction units 1211 and 1212 are inputted to the weight assigning unit 1213. Then, in the weight assigning unit 1213, a weighted average value of these two features is calculated. Specifically, the weight assigning unit 1213 may determine weights such that similar portions of the two features are relatively emphasized and dissimilar portions of the two features are relatively de-emphasized. That is, the weights may be determined in a way that the weights has higher values for the similar parts and lower values for the dissimilar parts. This allows the more important part of the two features to be emphasized, while the less important part may be removed or faded.

By providing the weight assigning unit 1213 according to one embodiment, the speech and the noise can be clearly separated even in the presence of loud noise. Thus, the STT model according to one embodiment may have a high speech recognition rate. Here, the determination and assignment of weights by the weight assigning unit 1213 may be based on an attention fusion technique, but is not limited thereto.

The weighted average value calculated by the weight assigning unit 1213 is inputted to the encoding vector generation unit 1214. The encoding vector generation unit 1214 is configured to generate and output, as an encoding vector, features of the residual part of the sound after the noise is removed from the sound containing the speech and the noise. That is, the input of the encoding vector generation unit 1214 is the weighted average value, and the output of the encoding vector generation unit 1214 is the encoding vector that is a vector obtained by encoding the features of the speech of the sound from which the noise has been removed.

The decoding part 123 receives the encoding vector generated and outputted by the encoding vector generation unit 1214 from the encoding part 122. Then, the decoding part 123 generates text such as a script from the encoding vector through a decoding process using a predetermined algorithm and outputs the generated text. Here, the process of generating and outputting the text such as the script from the encoding vector through the decoding process is a well-known technique. Thus, a detailed description thereof will be omitted.

Therefore, according to one embodiment, the features are extracted from the sound containing speech and noise and also from the refined result of such sound, the weighted average results are then derived for the extracted features, followed by the generation of encoding vectors from the weighted average result. Finally, the generated encoding vectors are decoded to obtain the text.

As a result, accurate speech recognition is achievable even in noisy environments. In other words, it is possible to implement a high-accuracy STT model (STT model with a high recognition rate) specifically designed for dentistry.

Hereinafter, the learning process of the STT model will be described in detail.

Figure 8:
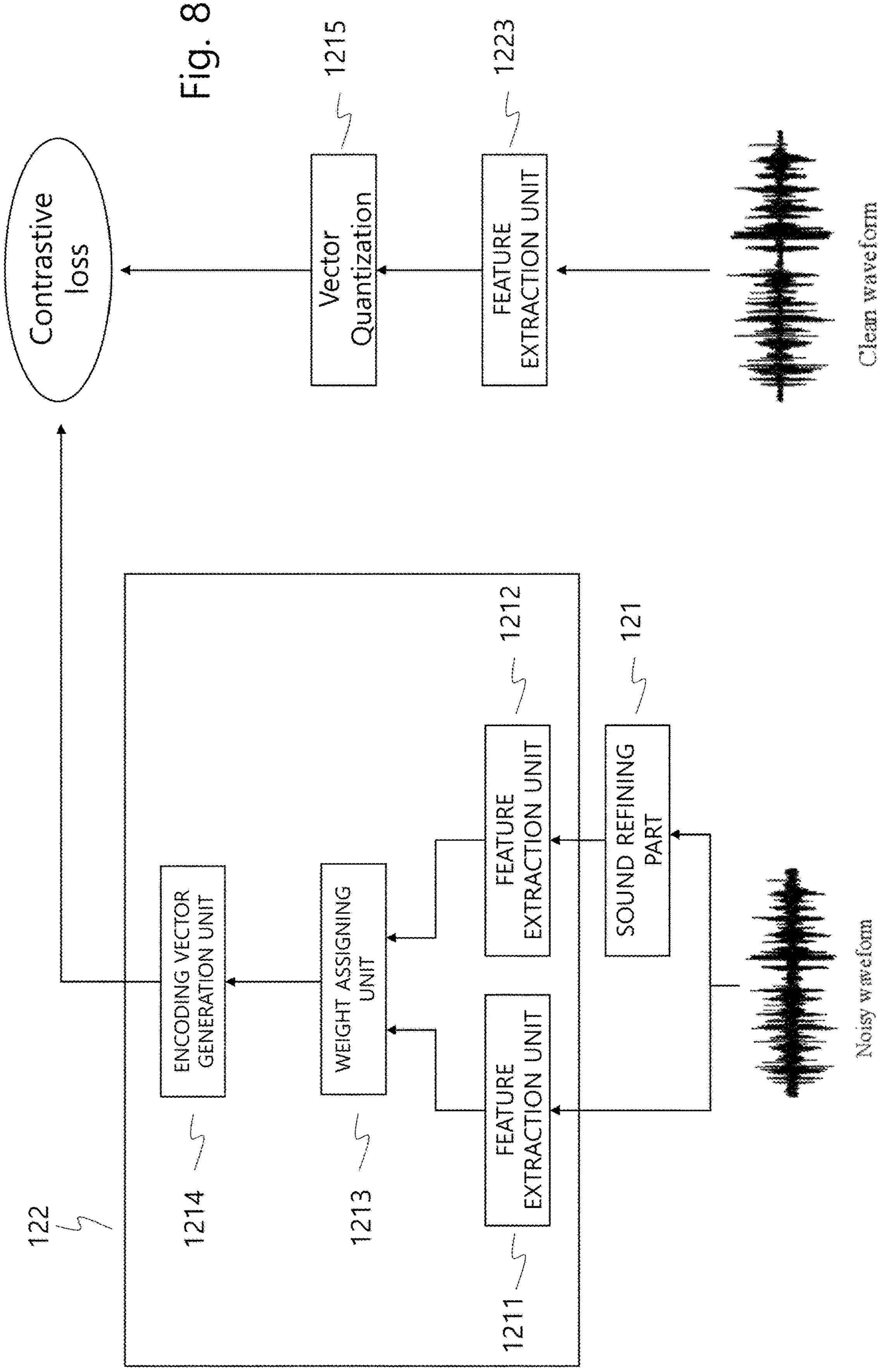
FIG. 8 conceptually illustrates a process for pre-training an encoding part of the STT model according to the embodiment of the present disclosure.
Figure 9:
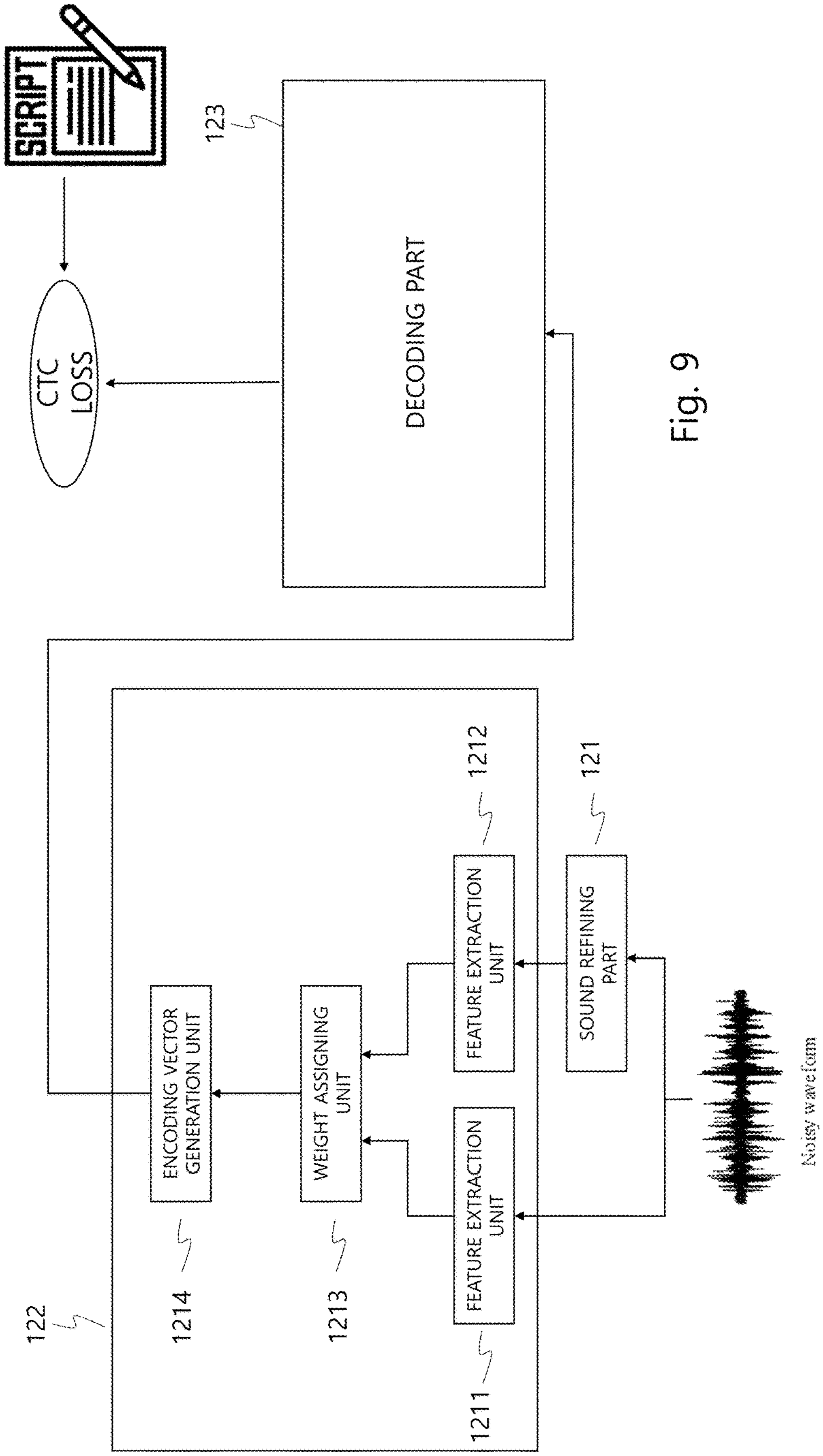
FIG. 9 conceptually illustrates a process for fine-tuning the STT model according to one embodiment of the present disclosure.
Figure 10:
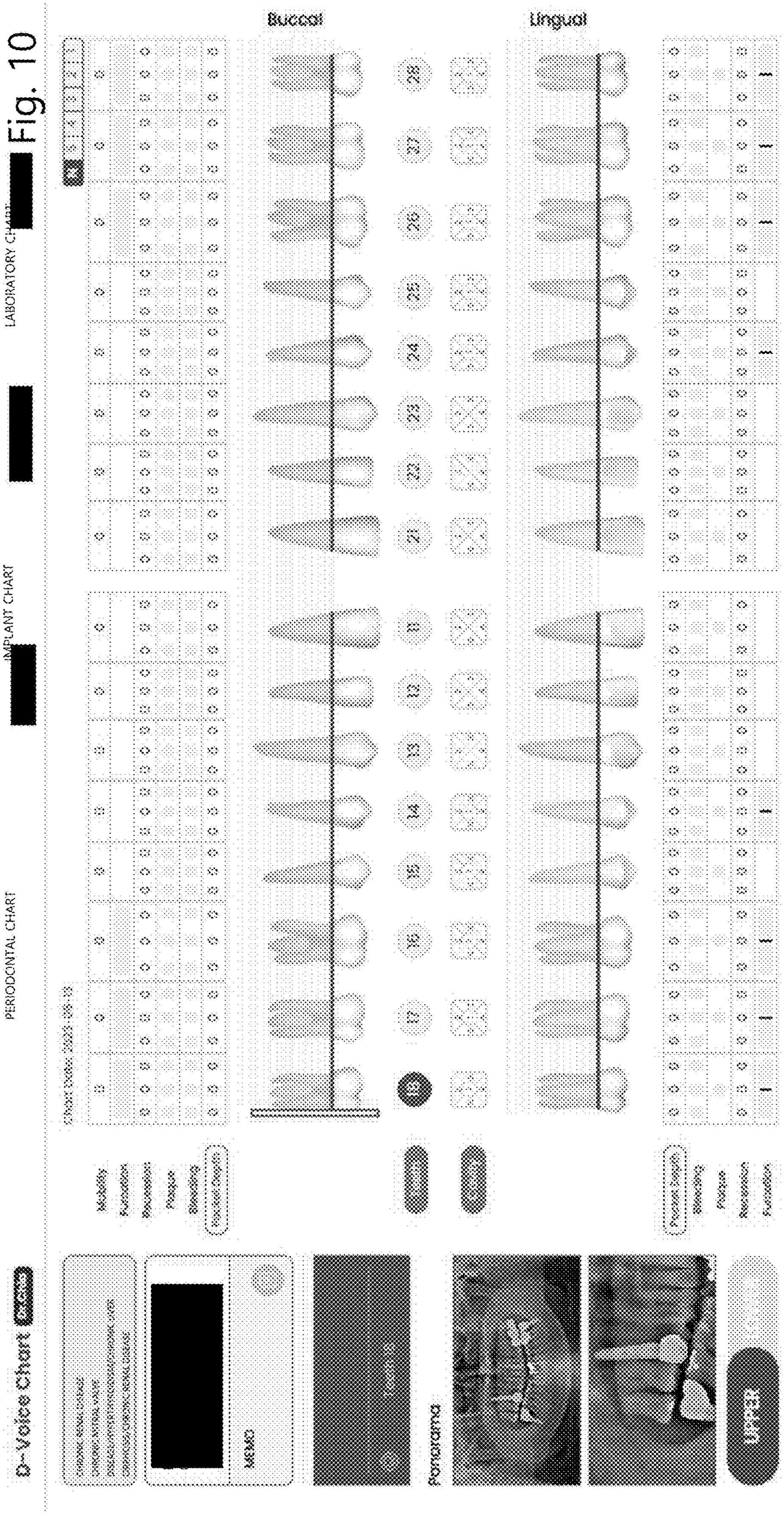
FIGS. 10 and 11 illustrate examples for implant charts.
Figure 11:
Figure 12:
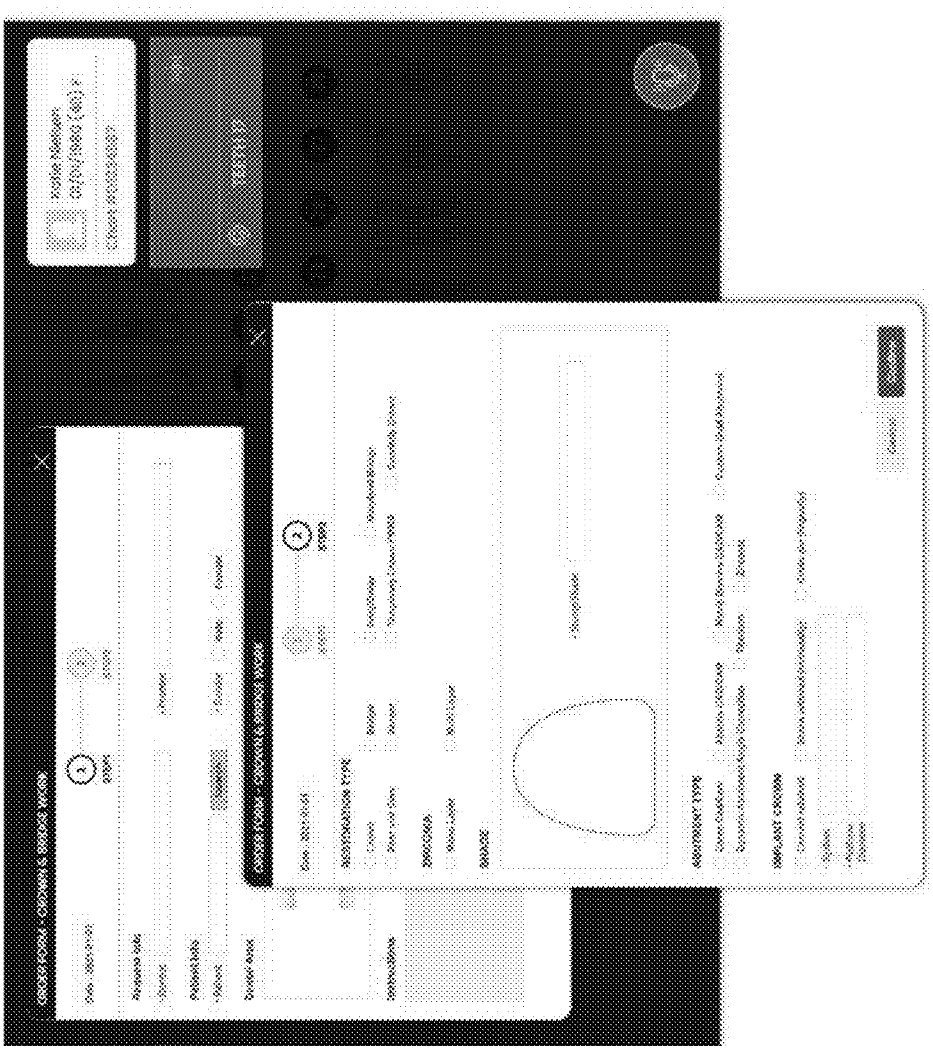
FIG. 12 illustrates an example of a laboratory chart.

FIGS. 8 and 9 illustrate an example of the learning process for the STT model according to one embodiment of the present disclosure. It should be noted that FIGS. 8 and 9 are merely examples, and the learning process of the STT model is not limited to those illustrated in FIGS. 8 and 9.

First, the STT model may be trained using one of a supervised learning method, a self-supervised learning method and an unsupervised learning method, or a combination of these methods. In the training of this STT model, a pre-training process and a fine-tuning process are performed.

In the pre-training process, a universal speech is used as training data. In other words, the training data used in the pre-training process is not limited to the speech that can be obtained at the dental clinic, but can be all kinds of speeches that can be obtained in everyday life.

Referring to FIG. 8, the pre-training process will be described in more detail. First, a universal speech without noise is obtained. This is illustrated as a clean waveform in FIG. 8. A plurality of the universal speeches can be easily acquired in daily life.

Noise can then be artificially added to the clean waveform, resulting in a noisy waveform. The noise is not limited to one type since there are various types of noise. Therefore, an infinite number of noisy waveforms can be obtained from a single universal speech.

In this way, training dataset required for the pre-training is prepared. In the training dataset, an input data for training is the noisy waveform, and a label data (target data) for training is the clean waveform.

Next, the input data for training is provided to the sound refining part 121 described above. Then, the noisy waveform is subjected to the noise cancelling process.

Next, the sound without the noise cancelling process and the sound with the noise cancelling process are respectively provided to the feature extraction unit 1211 and the feature extraction unit 1212 in the encoding part 122 shown in FIG. 8. In the feature extraction units 1211 and 1212, features are extracted from spectrograms that are obtained through the transformation as described above.

Next, the feature extracted from each of the feature extraction units 1211 and 1212 is provided to the weight assigning unit 1213. As a result, the weighted average value described above is calculated.

Next, the weighted average value is provided to the encoding vector generation unit 1214. The encoding vector is then generated as described above.

Meanwhile, the clean waveform serving as the label data for training is provided to a feature extraction unit 1223. A feature extracted from the feature extraction unit 1223 is provided to a vector quantization unit 1215, and vectors are generated from the vector quantization unit 1215. Here, the feature extraction unit 1223 may perform the same function as the feature extraction units 1211 and 1212. Further, the vector quantization unit 1215 may be configured to convert the feature extracted by the feature extraction unit 1223 into vectors.

Then, at least one of the sound refining part 121, the feature extraction units 1211 and 1212, the weight assigning unit 1213, and the encoding vector generation unit 1214 may be trained such that the difference between the encoding vector generated by the encoding vector generation unit 1214 and the vectors generated by the vector quantization unit 1215 is minimized. A backpropagation method may be used for training, but is not limited thereto. Here, the aforementioned difference may be contrastive loss. That is, during the training process, the training can be performed to minimize the contrastive loss.

Here, in the case where self-supervised learning is employed, vast amounts of training datasets are generated by adding noises to the universal speech, and these training datasets can be used for training. Here, the noise serves as a kind of masking. That is, during the pre-training process, the training is performed to accurately extract vectors for speech despite the masking such as noise.

Next, the fine-tuning process will be described in detail with reference to FIG. 9. After at least one of the encoding part 122 and the sound refining part 121 is trained by the universal speech during the pre-training process, the dental-specific STT model is then targeted and the dental-specific sound is used for fine-tuning. Since the pre-training has already been performed with the universal speech, it is not necessary to have the large number of dental sounds required to achieve a desired recognition rate, i.e., the large number of data for training.

As for training data for fine-tuning, an input data for training includes sounds generated in the dental clinic. Such sounds may be generated during the dental treatment and, more specifically, the sounds may include speeches and noises generated during the dental treatment. Further, a label data for training may be a text such as a script for these speeches.

As shown in FIG. 9, the sound generated in the dental clinic is provided as the input data for training. The script for the speech of the sound is then provided as the label data for training. Specifically, the sound with the noise cancelling process is provided to the feature extraction unit 1212 via the sound refining part 121, and the sound without the noise cancelling process is provided to the feature extraction unit 1211. Then, the encoding vector is generated after the sound is processed through other components (the weight assigning unit 1213 and the encoding vector generation unit 1214) of the encoding part 122 shown in FIG. 9. The encoding vector thus generated is provided to the decoding part 123. The decoding part 123 generates a script through a decoding process. The generated script is then compared to the script serving as the label data for training. After the comparison, at least one of the sound refining part 121, each component of the encoding part 122, and the decoding part 123 is trained in order to minimize a difference between the generated script and the script serving as the label data for training. The difference may be referred to as Connectionist Temporal Classification (CTC) loss.

In other words, according to the embodiment, the features are extracted from the sound containing speech and noise and also from the refined result of such sound; the weighted average result is derived for the extracted features; an encoding vector is generated from the weighted average result; and the generated encoding vector is decoded to obtain the text.

Therefore, the speech can be recognized accurately even in a noisy environment. That is, it is possible to implement the STT model for dentistry with a high recognition rate.

Meanwhile, in one embodiment, although not illustrated in FIGS. 6 and 9, a word correction model 124 shown in FIG. 5 may be used. The word correction model 124 is trained to recommend one of words in the dictionary as an input word if the input word is not in the dictionary. For example, 'n' consecutive words (where n is a natural number), including words that are not in the dictionary, can be inputted to the word correction model. Then, the word correction model recommends one of the words in the dictionary for the word that is not in the dictionary and outputs the one that recommended. Then, the word that is not in the dictionary and included in the script may be replaced with a word in the dictionary.

Here, the word correction model may be trained through a supervised learning method. For training, the input data for training may include a plurality of sets of 'n' words including words that are not in the dictionary. Further, the label data for training may include a plurality of words in the dictionary in which words that are not in the dictionary are replaced with words that are in the dictionary.

Here, the words that are not in the dictionary may be randomly generated. For example, words that are not in the dictionary may be created in a variety of ways, for example, by omitting one of the syllables that make up the word, by changing consonants, by changing vowels, and the like. Here, once created, they must be checked to see if they actually exist in the dictionary.

Further, the number 'n' described above may be any number such as three, but is not limited thereto.

While the above-described dental chart integrated management server 100 has been described on the premise that it is implemented in a server and the speech recognized by the user terminal 200 is provided to the dental chart integrated management server 100. However, the technical scope of the present disclosure is not limited thereto. For example, the dental chart integrated management server 100 described above may be implemented in the user terminal 200. In this case, the dental-specific STT model may be implemented in a memory included in the user terminal 200 and run by the execution of a processor included in the user terminal 200. Thus, an STT model with the same performance as described above may be implemented.

Referring back to FIG. 5, the chart generation unit 125 will be described in more detail. The chart generation unit 125 is implemented to generate a chart. The chart may be specifically for dental use, but is not limited thereto. For example, charts for other types of medical facilities, such as obstetrics and gynecology, dermatology, plastic surgery, or ophthalmology, can also be generated by the chart generation unit 125.

The chart generation unit 125 may create various types of charts. For instance, the periodontal chart, the implant chart, or the laboratory chart, as discussed above, may be generated by the chart generation unit 125.

Among these, the periodontal chart indicates the patient's periodontal health status. This chart may include various information such as the presence of bleeding in the gums, the degree of periodontal recession, or the spacing between teeth. Further, the implant chart may include the plan for which type of implant will be used for each patient. Further, the laboratory chart may include information on which implant products will be used based on the type of implant determined for each patient.

When text, such as a script, is obtained through the STT model shown in FIG. 5, the chart described above may be generated or modified by the chart generation unit 125 shown in FIG. 5 based on such text. For this purpose, the chart generation unit 125 may include a module that extracts commands (instructions) related to the creation or modification of the chart from the text and operates the chart creation or modification function based on the extracted commands. Using such a module, voice commands or the like necessary to create or modify a chart contained in the text may be extracted and recognized.

Regarding the creation of the periodontal chart, sounds containing speeches (voices) and noises generated during measurement of a periodontal status of a patient are provided to the STT model to obtain a first script for the speeches. Subsequently, the first script is incorporated into the creation of the periodontal chart by the chart generation unit 125.

Next, regarding the creation of the implant chart, sounds containing noises and speeches generated during discussion about the patient's implant type are provided to the STT model to obtain a second script for the speeches. Subsequently, at least some of the first script and the second script are incorporated into the creation of the implant chart by the chart generation unit 125.

Next, regarding the creation of the laboratory chart, sounds containing noises and speeches generated during the process of discussing and deciding on an implant product, such as a prosthesis, to be used for the planned implant type are provided to the STT model to obtain a third script for the speeches. Subsequently, at least some of the first script, the second script, and the third script are incorporated into the creation of the laboratory chart by the chart generation unit 125.

Meanwhile, the implant chart may include the determined implant type to be used for the patient. In one embodiment, information that can be utilized in determining the implant type may be provided in the form of a report. Hereinafter, the failure rate inference model 126 and the implant type recommendation model 127 shown in FIG. 5 will be described in more detail.

The failure rate inference model 126 may be trained to infer the failure rate of each of different implant types when implanted in a patient. The failure rate inference model 126 may receive information related to the patient as input. Specifically, inputs to the failure rate inference model 126 may include features extracted from the patient's periodontal chart and/or the patient's past dental treatment history, as well as personal information about the patient such as age, gender, or blood type.

When the aforementioned information is provided as input, the failure rate inference model 126 may infer the failure rate for each of the different implant types. For instance, if there are a total of 50 types of implants, the failure rate inference model 126 may infer the failure rate for each of these 50 types when features extracted from a particular patient's periodontal chart are inputted thereto. These failure rates can serve as a reference for the dental professionals in determining the most suitable implant type for the patient. Additionally, if an implant type with a high inferred failure rate must be used for the patient, the dental professionals may fully inform the patient and provide appropriate warnings. Thus, the dental professionals may be able to have a defense in potential future medical disputes or incidents. An example of the failure rates is illustrated in FIG. 13. Referring to FIG. 13, respective rows represent the different implant types that can be placed in a specific patient. In each row, the failure rate indicates the probability of failure if that particular type of implant is placed in the specific patient.

The failure rate inference model 126 may be trained using the supervised learning method. Further, input training data may include features extracted from the periodontal chart of each of multiple patients. Labeled training data may include information about the success or failure of the type of implant placed in each patient.

In addition to inferring the failure rate for each implant type, the failure rate inference model 126 described above may also provide a contribution ratio in percentage form of each cause of failure when there are two or more causes of failure for each implant type. For example, referring to FIG. 13, when "view" in a detail item of the second row is clicked, the contribution ratios of three causes of failure are displayed. The three causes and their respective contribution ratios to the failure are as follows, although this is merely illustrative:

Bone necrosis (45%)

Medical compromise (35%)

Mone loss due to improper combination of implant prosthesis and implant (19%)

To this end, in the training process of the failure rate inference model 126 described above, the labeled training data may include not only information on whether or not each implant type is failed but also information on the causes of failure for a preset number of implant types, for example, 100 implant types.

Referring back to FIG. 5, in one embodiment, the implant type recommendation model 127 is implemented. The implant type recommendation model 127 is trained to recommend the most appropriate implant type for each patient. The operation and training method of the implant type recommendation model 127 are similar in principle to the failure rate inference model 126. Specifically, it is initially trained using the supervised learning method. Further, input training data may include features extracted from the periodontal chart of each of multiple patients. Labeled training data may include information about the type of implant placed in each patient. When the features extracted from a specific patient's periodontal chart are provided as input to the completely trained model 127, the model 127 may recommend the most appropriate implant type for the specific patient from a plurality of preset implant types.

However, the type of implant recommended by the implant type recommendation model 127 is not entirely related to the success rate. This is because the data used to train the implant type recommendation model 127 is the frequency of implant types actually placed in each patient, not whether the implant types were successful or failed. Depending on the embodiment, the data used to train the implant type recommendation model 127 may include information about the type of implant determined by the failure rate inference model 126 to have the lowest failure rate, or information about the type of implant actually placed in the patient after discussion by the dental professionals.

Therefore, in one embodiment, when features are extracted from a patient's periodontal chart and an implant type for the patient is recommended by the implant type recommendation model 127 based on the extracted features, the risk or failure rate of the recommended implant type can be verified. For example, the failure rate for the implant type recommended by the implant type recommendation model 127 may be verified from the failure rate inferred by the failure rate inference model 126 described above. If the failure rate of the recommended implant type, as inferred by the failure rate inference model 126, exceeds a predetermined threshold, a warning may be issued regarding placing the recommended implant type in the patient.

Referring back to FIG. 5, the implant product ordering unit 128 is implemented. This implant product ordering unit 128 is configured to facilitate the ordering of necessary implant products by each dental clinic based on implant type. When an order is placed through the implant product ordering unit 128, the required implant products can be supplied to each dental clinic accordingly.

Figure 17:
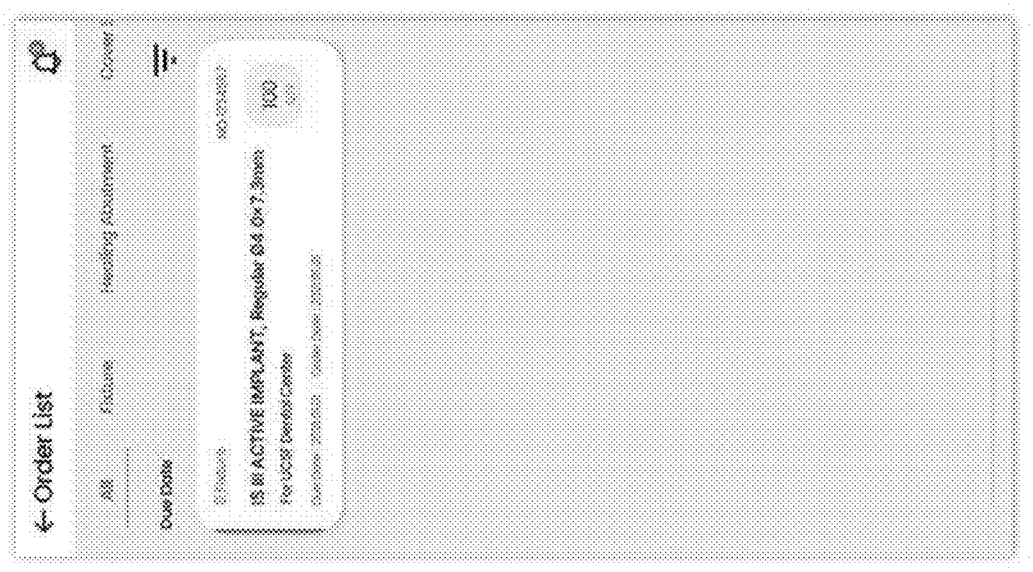

Specifically, when the aforementioned laboratory chart is generated, it may be determined which implant products, such as prosthetics, will be used according to the implant plan. During this process, the inventory of the prosthetics may be depleted. Therefore, the implant product ordering unit 128 may operate to monitor the inventory levels of implant products based on the types and quantities of implant products listed in the laboratory chart, and to place orders for the necessary implant products if needed. For instance, the inventory levels of each implant product may be updated in real-time within the implant product ordering unit 128. These inventory levels may be inputted from a terminal operated by the dental clinic, such as, but not limited to, the user terminal 200. Additionally, the implant product ordering unit 128 may acquire information about the types and quantities of implant products listed in the laboratory chart. Based on this acquired information, the implant product ordering unit 128 may determine the estimated inventory levels for each implant product at the dental clinic after a predetermined period. If the estimated inventory level falls below a predetermined threshold, the implant product ordering unit 128 may operate to place an order for the necessary implant products. For example, the implant product ordering unit 128 may operate to display a message on the user terminal 200 indicating that an order is needed for such implant products, or to automatically place an order with the implant solution provider through the implant solution provider server 400 according to a predefined algorithm or routine. The status of such orders is exemplarily illustrated in FIG. 17.

Furthermore, the estimated inventory levels for each implant product can be predicted using deep neural networks such as recurrent neural networks (RNN).

Figure 14:
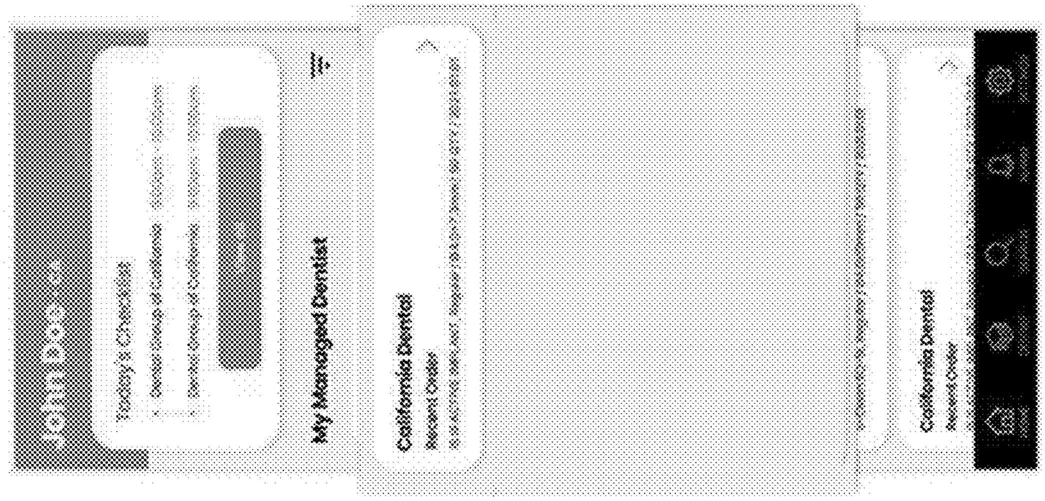
FIG. 14 conceptually illustrates that an implant surgery history for each of dental practitioners is provided according to one embodiment of the present disclosure.
Figure 15:
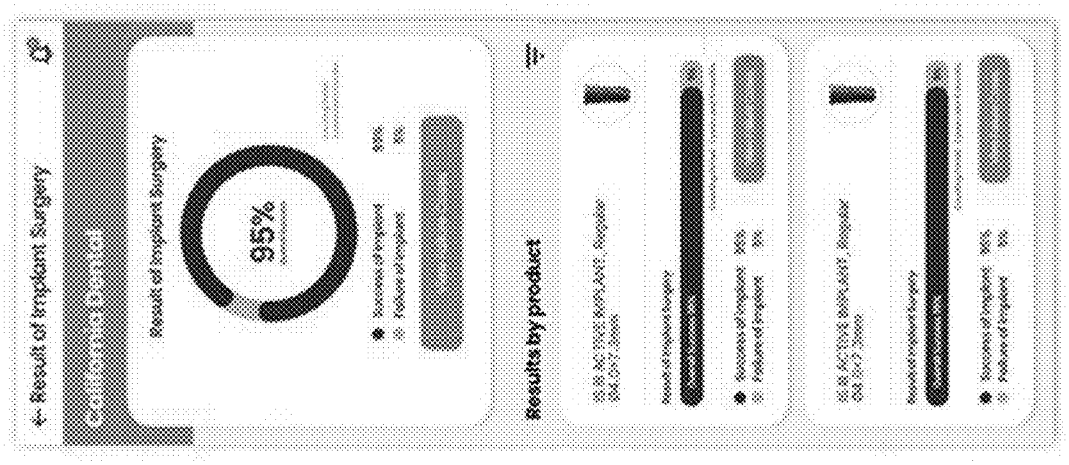
FIG. 15 conceptually illustrates that statistics of procedure failure rate or success rate for each of implant solutions provided by an implant solution provider is provided as statistics according to one embodiment of the present disclosure.
Figure 16:
FIGS. 16 and 17 illustrate examples of lists of implant products ordered by respective dental clinics and provided from the implant solution provider according to one embodiment of the present disclosure.

Additionally, the failure rate for each implant type described above may be generated for each dental clinic or for an individual dentist within each clinic. Information or statistics on which implant types are being administered to patients or which implant products are being consumed in each dental clinic may also be generated for each dental clinic or for each dentist. The information or statistics thus generated are exemplarily shown in FIGS. 14 and 15. This information or statistics may be provided to the dental clinics or the implant solution providers through the user terminal 200.

As described above, according to one embodiment, various types of charts generated in dental clinics can be easily created and managed using an advanced STT model. Additionally, information necessary for determining the contents to be recorded in these charts, such as information used to determine the type of implant to be applied to a patient, can be provided. Furthermore, various types of information that can be useful for dental professionals or implant solution providers can also be provided in the form of reports.

Figure 18:
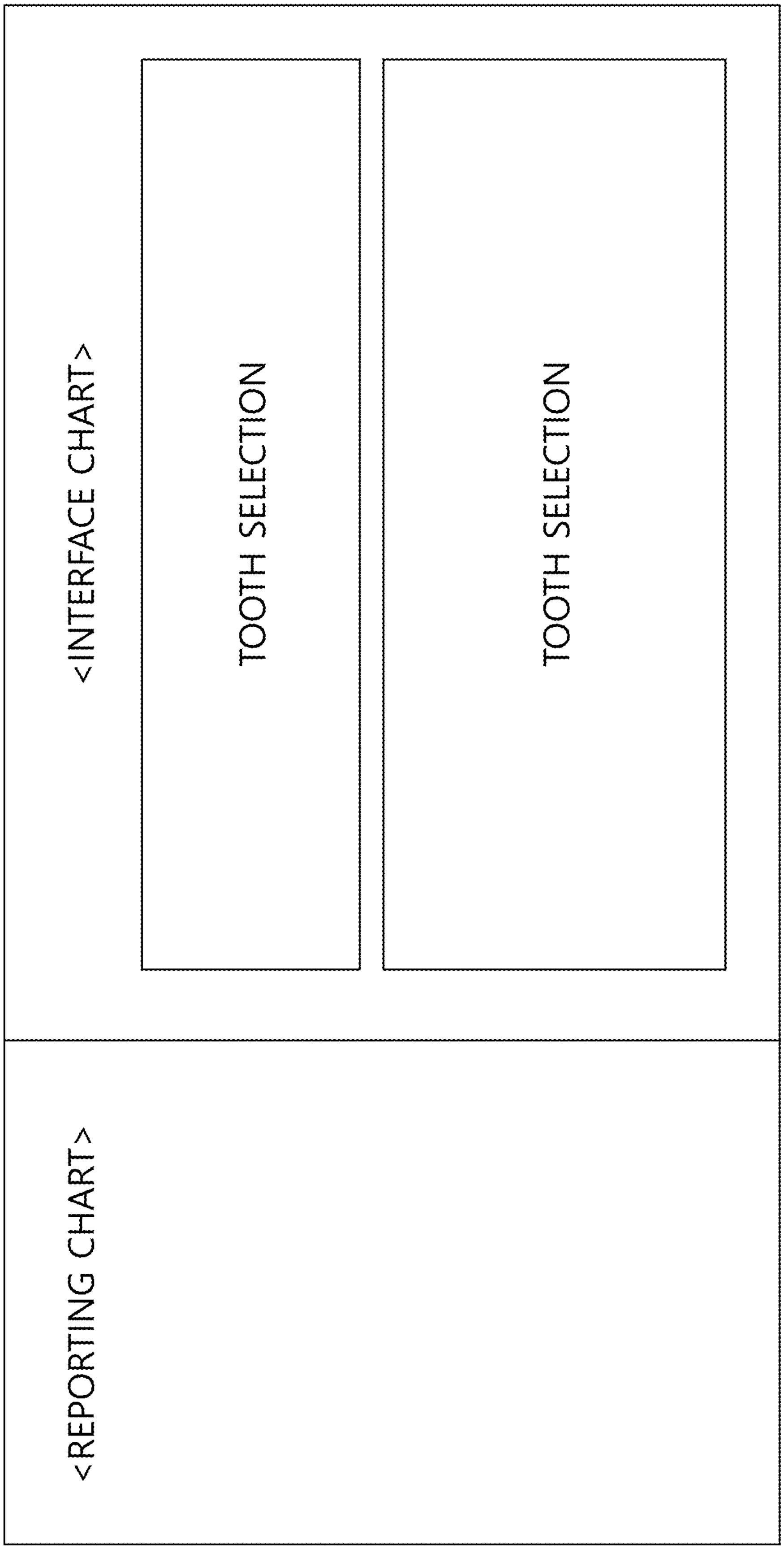
FIG. 18 conceptually illustrates an example of each chart that includes an interface chart and a reporting chart according to one embodiment of the present disclosure.

In one embodiment, each of the aforementioned charts, such as the periodontal chart, the implant chart, and the laboratory chart, may be configured to include both an interface chart and a reporting chart, as shown in FIG. 18.

Specifically, each of the periodontal chart, the implant chart, and the laboratory chart may include a reporting chart on the left and an interface chart on the right. However, the arrangement of the reporting chart and the interface chart is not limited thereto.

As shown in FIG. 18, the reporting chart may have a form similar or identical to a general electronic chart. However, for medical professionals who intend to create charts using the speeches (voices), it may not be easy to provide voice commands or have the necessary information written down while only looking at the reporting chart. This is because the reporting chart is designed for clear and concise viewing in view of checking the chart, not for ease of input using voice commands.

Thus, in one embodiment, there may be provided a separate interface chart that is designed to facilitate the selection of each item through voice commands and further to facilitate the input of content for each selected item. Referring to FIG. 18, the interface chart according to one embodiment may include a section for displaying teeth and an item input section for inputting a description of the selected teeth. Further, in the item input section, multiple items may be listed in a predetermined order. This ordering may be designed to facilitate selection and input by the user, i.e., the medical professional, who will fill out the chart using voice commands. In other words, this interface chart serves as a template for chart creation.

In this case, the aforementioned memory 120 may store a selection instruction for selecting each of these items.

If a medical professional utters a specific selection instruction to select a particular item and the script recognized in the uttered voice contains the selection instruction, the item corresponding to the selection instruction is selected. Following this, based on the subsequent voice input, the contents for the selected item are described and recorded. Thus, by using the interface chart, which serves as a template, the creation of charts can be performed more smoothly and quickly.

Here, the aforementioned items may include, for example, but not limited to, diagnosis, Tx. Plan, Bone Density, and the like.

In one embodiment, each time a selection instruction for selecting an item is uttered and recognized by a user, including a medical professional, these selection instructions are stored cumulatively. These selection instructions are important commands for chart creation. Therefore, it is desirable to have a high recognition rate for those instructions. In one embodiment, the actually spoken and recognized selection instructions may be stored separately and cumulatively for use in training the STT model described above, and more specifically, for fine-tuning the STT model. That is, the accumulated selection instructions may be used to retrain or update the fine-tuning of the STT model. Thus, the recognition accuracy of the instructions for selecting each item in the STT model may be improved.

The foregoing has described the dental chart integration management server 100 according to one embodiment of the present disclosure. Hereinafter, an integrated management method for a dental chart performed by the dental chart integrated management server 100 will be described.

Figure 19:
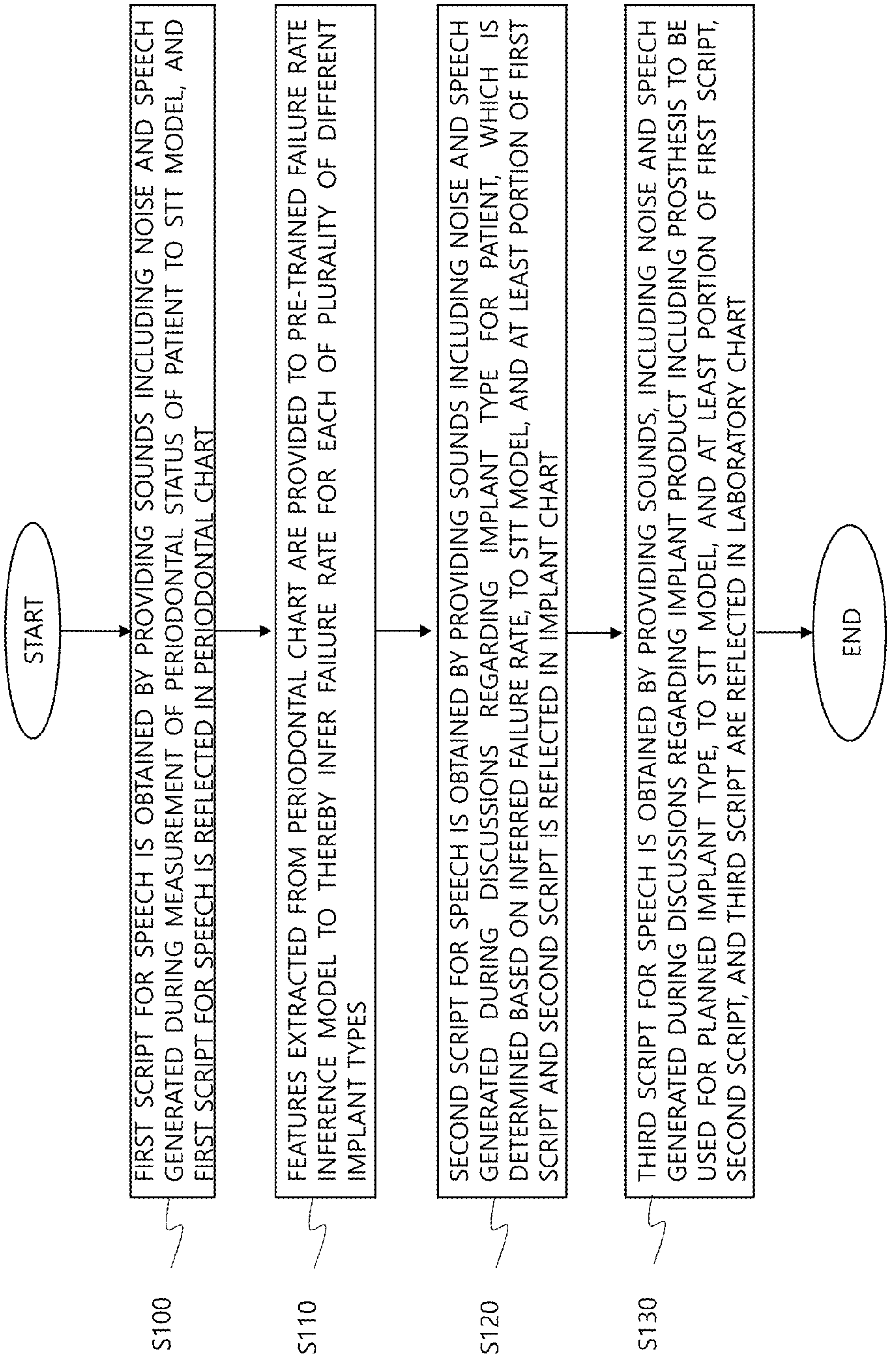
FIG. 19 illustrates an exemplary flowchart of an integrated management method for a dental chart according to one embodiment of the present disclosure.

FIG. 19 illustrates an exemplary flowchart of an integrated management method for a dental chart according to one embodiment of the present disclosure. It should be noted that this flowchart is exemplary only, and the scope of the present disclosure is not limited thereto. For example, depending on the embodiment, steps may be performed in a different order from that shown in FIG. 19, at least one step that is not shown in FIG. 19 may be additionally performed, or at least one of the steps shown in FIG. 19 may not be performed.

Referring to FIG. 19, in step S100, when sounds including noise and speech generated during measurement of a periodontal status of a patient is provided to the STT model and a first script for the speech is obtained, the first script is reflected in (incorporated into) a periodontal chart. The STT model mentioned here has been described previously, thus description of the STT model will be omitted herein.

Further, in step S110, features extracted from the periodontal chart are provided to a pre-trained failure rate inference model to thereby infer a failure rate for each of a plurality of different implant types.

Further, in step S120, when sounds including noise and speech generated during discussions regarding the implant type for the patient, which is determined based on the inferred failure rate, is provided to the STT model and a second script for the speech is obtained, at least a portion of the first script and the second script is reflected in an implant chart.

Further, in step S130, when sounds, including noise and speech generated during discussions regarding an implant product including a prosthesis to be used for the planned implant type, is provided to the STT model and a third script for the speech is obtained, at least a portion of the first script, the second script, and the third script are reflected in a laboratory chart.

The above-described method is performed by the dental chart integrated management server 100 described above, redundant description thereof will be omitted.

The method according to the various embodiments described above may also be implemented in the form of a computer program stored on a computer-readable storage medium programmed to perform each of the steps of the method, and may also be implemented in the form of a computer-readable storage medium storing a computer program programmed to perform each of the steps of the method.

The above description illustrates the technical idea of the present disclosure, and it will be understood by those skilled in the art to which this present disclosure belongs that various changes and modifications may be made without departing from the scope of the essential characteristics of the present disclosure. Therefore, the exemplary embodiments disclosed herein are not used to limit the technical idea of the present disclosure, but to explain the present disclosure, and the scope of the technical idea of the present disclosure is not limited by those embodiments. Therefore, the scope of protection of the present disclosure should be construed as defined in the following claims, and all technical ideas that fall within the technical idea of the present disclosure are intended to be embraced by the scope of the claims of the present disclosure.

What is claimed is:

1. An integrated management system for a dental chart, comprising:

an encoding unit configured to receive and encode waveforms that contain sounds containing noises and speeches, wherein the encoding unit is trained using multiple sounds containing speeches and noises through a pre-training process included in the speech-to-text (STT) model;

a decoding unit configured to decode a generated encoding vector and generate the scripts for the speeches;

a memory that stores one or more instructions; and a processor, wherein the memory includes the STT model that, when said sounds containing noises and speeches are obtained and a noise cancelling process is performed on the obtained sounds, executes a process of extracting and processing features from the sounds with the noise cancelling process and the sounds without the noise cancelling process and a process of obtaining scripts for the speeches, wherein the one or more instructions, when executed by the processor, cause the processor to perform operations including:

providing, by the processor, first said sounds containing noises and speeches, which are generated during measurement of a periodontal status of a patient, to the STT model, obtaining, by the processor, a first script for the speeches, and generating, by the processor, a periodontal chart based on the first script, providing, by the processor, features extracted from the periodontal chart to a pre-trained failure rate inference model for each implant type to infer a failure rate for each of a plurality of different implant types, providing, by the processor, second said sounds containing noises and speeches generated during discussions regarding an implant type of the patient, which is determined based on the inferred failure rate, to the STT model,—obtaining, by the processor, a second script for the speeches and generating, by the processor, an implant chart based on at least a portion of the first script and the second script, providing, by the processor, third said sounds containing noises and speeches, which are generated during discussions regarding an implant product including a prosthesis to be used for the determined implant type of the patient, to the STT model, obtaining, by the processor, a third script for the speeches and generating, by the processor, a laboratory chart based on at least a portion of the first script, the second script, and the third script, displaying, through a display device, at least one of the periodontal chart, the implant chart, and the laboratory chart, wherein, in the process of extracting the features from the sound with the noise cancelling process and the features from the sound without the noise cancelling process, each of the sound with the noise cancelling process and the sound without the noise cancelling process is converted into a spectrogram, and the features are extracted from the corresponding spectrogram by using a convolutional neural network, wherein clean waveforms generated based on said extracted features from the sounds with the noise cancelling process and the sound without the noise cancelling process are utilized by the STT model to distinguish noises from speeches and obtain said first, second, and third scripts, and wherein in a fine-tuning process included in training of the STT model, multiple sounds containing noises and speeches that are generated during a dental treatment, and a script for each of the multiple sounds are used as training data.

2. The integrated management system for the dental chart as claimed in claim 1, wherein the noise cancelling process is performed by a model that performs speech enhancement.

3. The integrated management system for the dental chart as claimed in claim 1, wherein, in the process of extracting the features from the sounds with the noise cancelling process and the features from the sounds without the noise cancelling process, each of the sounds with the noise cancelling process and the sounds without the noise cancelling process is converted into a spectrogram, and the features are extracted from the corresponding spectrogram by using a convolutional neural network.

4. The integrated management system for the dental chart as claimed in claim 1, wherein a weight is assigned such that a relatively higher weight value is assigned to a part that is relatively similar and a relatively lower weight value is assigned to a part that is not relatively similar between the sounds with the noise cancelling process and the sounds without the noise cancelling process.

5. The integrated management system for the dental chart as claimed in claim 1, wherein an encoding part included in the STT model obtains an encoding vector as a result of the processing, and the encoding part is trained using multiple sounds containing speeches and noises through a pre-training process included in the STT model.

6. The integrated management system for the dental chart as claimed in claim 5, wherein a decoding part included in the STT model performs the process of obtaining the scripts for the speeches by decoding the obtained encoding vector, and in the fine-tuning process, a training is performed such that a difference between a result outputted from the decoding part and the scripts serving as the training data is minimized, the result being outputted in response to the encoding part being provided with the multiple sounds containing the noises and the speeches generated during the dental treatment.

7. The integrated management system for the dental chart as claimed in claim 6, wherein connectionist temporal classification (CTC) loss is used for the training performed to minimize the difference between the result outputted from the decoding part and the scripts serving as the training data.

8. The integrated management system for the dental chart as claimed in claim 1, wherein the one or more instructions, when executed by the processor, cause the processor to provide, if the scripts includes a word that is not in a dictionary, three consecutive words including the word that is not in the dictionary to a trained word correction model, and wherein the word that is not in the dictionary is replaced with a word corrected by the trained word correction model.

9. The integrated management system for the dental chart as claimed in claim 1, wherein the failure rate inference model for each implant type is trained to provide a contribution ratio of each cause of failure when there are two or more causes of failure for each implant type.

10. The integrated management system for the dental chart as claimed in claim 1, wherein the memory further include an implant type recommendation model, and each time an implant type is determined for the patient, features extracted from the periodontal chart of the patient are used as input training data and the determined implant type for the patient is used as labeled training data to train the implant type recommendation model.

11. The integrated management system for the dental chart as claimed in claim 10, wherein when a periodontal chart is generated for a new patient from measurement of a periodontal status of the new patient, the failure rate inference model for each implant is used to infer the failure rate for each of the plurality of different implant types type, and the implant type recommendation model is used to recommend an implant type for the new patient by using features extracted from the periodontal chart generated for the new patient, and a warning is issued regarding the recommended implant type for the new patient in response to a case where the failure rate inferred by the failure rate inference model for the implant type recommended to the new patient exceeds a predetermined threshold.

12. The integrated management system for the dental chart as claimed in claim 1, wherein an order for the implant product is generated or not generated depending on types and quantities of implant products listed in the laboratory chart.

13. The integrated management system for the dental chart as claimed in claim 1, wherein statistics on types of implants placed in patients and the failure rate for each implant type are generated for each dental clinic or an individual dentist in each dental clinic.

14. The integrated management system for the dental chart as claimed in claim 1, wherein each of the periodontal chart, the implant chart, and the laboratory chart includes an interface chart through which one of a plurality of items is selected according to voice input or content for the selected item is recorded by reflecting the voice input, and a reporting chart that is dependently generated based on the content of the interface chart.

15. The integrated management system for the dental chart as claimed in claim 14, wherein the memory stores a selection instruction for each of the plurality of items, and wherein the one or more instructions, when executed by the processor, cause the processor to select, when the selection instruction is recognized from a script obtained from the voice input, the item corresponding to the recognized selection instruction.

16. The integrated management system for the dental chart as claimed in claim 15, wherein the memory stores recognized selection instructions cumulatively each time the selection instruction is recognized, and wherein the one or more instructions, when executed by the processor, cause the processor to retrain the fine-tuning included in the training of the STT model using the cumulatively stored selection instructions.

17. An integrated management method for a dental chart that is performed by an integrated management server for the dental chart including a memory that stores a speech-to-text (STT) model that, when sounds containing noises and speeches are obtained and a noise cancelling process is performed on the obtained sounds, executes a process of extracting and processing features from the sounds with the noise cancelling process and the sounds without the noise cancelling process and a process of obtaining scripts for the speeches, the integrated management method comprising:

encoding, by an encoding unit, waveforms that contain the sounds containing noises and speeches, wherein the encoding unit is trained through a pre-training process included in the STT model;

providing, by the integrated management server, first said sounds containing noises and speeches, which are generated during measurement of a periodontal status of a patient, to the STT model, obtaining, by the integrated management server, a first script for the speeches and generating, by the integrated management server, a periodontal chart based on the first script, providing, by the integrated management server, features extracted from the periodontal chart to a pre-trained failure rate inference model for each implant type to infer a failure rate for each of a plurality of different implant types, providing, by the integrated management server, second said sounds containing noises and speeches generated during discussions regarding an implant type of the patient, which is determined based on the inferred failure rate, to the STT model, obtaining, by the integrated management server, a second script for the speeches and generating, by the integrated management server, an implant chart based on at least a portion of the first script and the second script, providing, by the integrated management server, third said sounds containing noises and speeches, which are generated during discussions regarding an implant product including a prosthesis to be used for the determined implant type of the patient, to the STT model, obtaining, by the integrated management server, a third script for the speeches and generating, by the integrated management server, a laboratory chart based on at least a portion of the first script, the second script, and the third script, and displaying, through a display device, at least one of the periodontal chart, the implant chart, and the laboratory chart, wherein, in the process of extracting the features from the sound with the noise cancelling process and the features from the sound without the noise cancelling process, each of the sound with the noise cancelling process and the sound without the noise cancelling process is converted into a spectrogram, and the features are extracted from the corresponding spectrogram by using a convolutional neural network, wherein clean waveforms generated based on said extracted features from the sounds with the noise cancelling process and the sounds without the noise cancelling process are utilized by the STT model to distinguish noises from speeches and obtain said first, second, and third scripts, and wherein in a fine-tuning process included in training of the STT model, the sounds containing noises and speeches that are generated during a dental treatment, and a script for each of the multiple sounds, are used as training data.

18. The integrated management method for the dental chart as claimed in claim 17, wherein the noise cancelling process is performed by a model that performs speech enhancement.

19. A non-transitory computer-readable storage medium that stores a computer program including one or more instructions that, when executed by a processor of a computer, cause the computer to perform steps in the integrated management method as claimed in claim 17.

* * * * *